(12) United States Patent
Wysocki et al.

(10) Patent No.: US 7,875,078 B2
(45) Date of Patent: *Jan. 25, 2011

(54) EXPANDABLE INTERBODY FUSION DEVICE

(75) Inventors: Steve Wysocki, Stratford, CT (US);
Joseph N. Logan, Trumbull, CT (US);
Richard Manzi, Yorktown Heights, NY (US); Robert D. Paxson, Lakeland, TN (US); John Pafford, Eads, TN (US);
Mark D. LoGuidice, Southport, CT (US); Tyler P. Lipschultz, New Canaan, CT (US); Carl Michael Nilsson, Cleveland Heights, OH (US); Daniel S. Savage, Brecksville, OH (US)

(73) Assignee: Spine Wave, Inc., Shelton, CT (US)

( * ) Notice: Subject to any disclaimer, the term of this patent is extended or adjusted under 35 U.S.C. 154(b) by 1553 days.

This patent is subject to a terminal disclaimer.

(21) Appl. No.: 11/211,347

(22) Filed: Aug. 25, 2005

(65) Prior Publication Data
US 2006/0058880 A1 Mar. 16, 2006

Related U.S. Application Data

(60) Provisional application No. 60/604,422, filed on Aug. 25, 2004.

(51) Int. Cl.
*A61F 2/44* (2006.01)
(52) U.S. Cl. .................. 623/17.15; 623/17.16; 606/90
(58) Field of Classification Search ... 623/17.11–17.16; 606/53, 60, 245, 90, 99
See application file for complete search history.

(56) References Cited

U.S. PATENT DOCUMENTS 3,486,505 A 12/1969 Morrison (Continued)

FOREIGN PATENT DOCUMENTS

EP 0621020 10/1994

(Continued)

OTHER PUBLICATIONS

Medtronic Sofamor Danek, Verte-Stack PEEK Stackable Corpectomy Device, Surgical Technique (date unknown), 8 pages.

(Continued)

*Primary Examiner*—Eduardo C Robert
*Assistant Examiner*—Lynnsy Schneider
(74) *Attorney, Agent, or Firm*—Hoffman & Baron, LLP

(57) ABSTRACT

An expandable interbody fusion device for implantation into the intradiscal space between two opposing vertebral bodies of a spine comprises a superior endplate member having an upper surface for engaging a superior vertebral body in a spine, and an inferior endplate member having a lower surface for engaging an inferior vertebral body in the spine. The superior endplate member and the inferior endplate member are releasably coupled and define a cavity therebetween. At least one expansion member is configured to be introduced into the cavity to move the superior endplate and the inferior endplate members relatively apart upon introduction and to thereby decouple the superior endplate member and the inferior endplate member. An inserter may be releasably coupled to the device to facilitate insertion of the device as well as to provide a track for insertion of the expansion members.

26 Claims, 31 Drawing Sheets

U.S. PATENT DOCUMENTS

| | | | |
|---|---|---|---|
| 4,524,766 A | 6/1985 | Petersen | |
| 4,683,476 A | 7/1987 | Ferrari et al. | |
| 4,736,738 A | 4/1988 | Lipovsek et al. | |
| 4,755,797 A | 7/1988 | Kanaya | |
| 4,863,476 A | 9/1989 | Shepperd | |
| 4,888,024 A | 12/1989 | Powlan | |
| 5,059,193 A | 10/1991 | Kuslich | |
| 5,192,326 A | 3/1993 | Bao et al. | |
| 5,192,327 A | 3/1993 | Brantigan | |
| 5,197,971 A | 3/1993 | Bonutti | |
| 5,290,312 A * | 3/1994 | Kojimoto et al. | 623/17.15 |
| 5,298,254 A | 3/1994 | Prewett et al. | |
| 5,431,658 A | 7/1995 | Moskovich | |
| 5,439,684 A | 8/1995 | Prewett et al. | |
| 5,505,732 A | 4/1996 | Michelson | |
| 5,514,180 A | 5/1996 | Heggeness et al. | |
| 5,522,899 A | 6/1996 | Michelson | |
| 5,571,109 A | 11/1996 | Bertagnoli | |
| 5,591,235 A | 1/1997 | Kuslich | |
| 5,645,599 A | 7/1997 | Samani | |
| 5,702,454 A | 12/1997 | Baumgartner | |
| 5,755,797 A | 5/1998 | Baumgartner | |
| 5,756,127 A | 5/1998 | Grisoni et al. | |
| 5,836,948 A | 11/1998 | Zucherman et al. | |
| 5,860,977 A | 1/1999 | Zucherman et al. | |
| 5,888,228 A * | 3/1999 | Knothe et al. | 623/17.16 |
| 5,891,147 A | 4/1999 | Moskovitz et al. | |
| 5,951,553 A | 9/1999 | Betz et al. | |
| 5,980,522 A * | 11/1999 | Koros et al. | 623/17.11 |
| 6,033,411 A | 3/2000 | Preissman | |
| 6,045,579 A | 4/2000 | Hochshuler et al. | |
| 6,066,154 A | 5/2000 | Reiley et al. | |
| 6,074,390 A | 6/2000 | Zucherman et al. | |
| 6,110,179 A | 8/2000 | Flivik et al. | |
| 6,110,210 A | 8/2000 | Norton et al. | |
| 6,159,211 A | 12/2000 | Boriani et al. | |
| 6,159,244 A | 12/2000 | Suddaby | |
| 6,190,414 B1 | 2/2001 | Young et al. | |
| 6,193,757 B1 * | 2/2001 | Foley et al. | 623/17.16 |
| 6,200,347 B1 | 3/2001 | Anderson et al. | |
| 6,241,771 B1 | 6/2001 | Gresser et al. | |
| 6,273,916 B1 | 8/2001 | Murphy | |
| 6,279,916 B1 | 8/2001 | Stecher | |
| 6,287,308 B1 | 9/2001 | Betz et al. | |
| 6,287,309 B1 | 9/2001 | Baccelli et al. | |
| 6,387,130 B1 | 5/2002 | Stone et al. | |
| 6,395,034 B1 | 5/2002 | Suddaby | |
| 6,402,750 B1 | 6/2002 | Atkinson et al. | |
| 6,419,705 B1 * | 7/2002 | Erickson | 623/17.16 |
| 6,432,107 B1 | 8/2002 | Ferree | |
| 6,436,142 B1 | 8/2002 | Paes et al. | |
| 6,478,800 B1 | 11/2002 | Fraser et al. | |
| 6,488,710 B2 | 12/2002 | Besselink | |
| 6,500,205 B1 | 12/2002 | Michelson | |
| 6,562,074 B2 * | 5/2003 | Gerbec et al. | 623/17.15 |
| 6,595,998 B2 * | 7/2003 | Johnson et al. | 606/90 |
| 6,620,196 B1 | 9/2003 | Trieu | |
| 6,648,917 B2 | 11/2003 | Gerbec et al. | |
| 6,656,178 B1 | 12/2003 | Veldhuizen et al. | |
| 6,726,691 B2 | 4/2004 | Osorio et al. | |
| 6,740,093 B2 | 5/2004 | Hochschuler et al. | |
| 6,830,589 B2 * | 12/2004 | Erickson | 623/17.15 |
| 6,837,904 B2 | 1/2005 | Ralph et al. | |
| 6,852,095 B1 | 2/2005 | Ray | |
| 6,852,126 B2 | 2/2005 | Ahlgren | |
| 6,852,129 B2 | 2/2005 | Gerbec et al. | |
| 6,855,167 B2 * | 2/2005 | Shimp et al. | 623/17.11 |
| 6,863,673 B2 | 3/2005 | Gerbec et al. | |
| 6,997,929 B2 * | 2/2006 | Manzi et al. | 606/90 |
| 7,094,257 B2 * | 8/2006 | Mujwid et al. | 623/17.15 |
| 7,118,580 B1 * | 10/2006 | Beyersdorff et al. | 606/99 |
| 7,220,280 B2 * | 5/2007 | Kast et al. | 623/17.11 |
| 7,235,101 B2 * | 6/2007 | Berry et al. | 623/17.11 |
| 7,500,992 B2 * | 3/2009 | Li | 623/17.11 |
| 7,618,458 B2 | 11/2009 | Biedermann et al. | |
| 2002/0010511 A1 * | 1/2002 | Michelson | 623/17.15 |
| 2002/0026195 A1 | 2/2002 | Layne et al. | |
| 2002/0062153 A1 * | 5/2002 | Paul et al. | 623/17.11 |
| 2002/0147497 A1 | 10/2002 | Belef et al. | |
| 2002/0177897 A1 | 11/2002 | Michelson | |
| 2003/0105528 A1 * | 6/2003 | Shimp et al. | 623/17.16 |
| 2003/0171812 A1 * | 9/2003 | Grunberg et al. | 623/17.11 |
| 2003/0199980 A1 * | 10/2003 | Siedler | 623/17.11 |
| 2004/0019354 A1 | 1/2004 | Johnson et al. | |
| 2004/0064144 A1 | 4/2004 | Johnson et al. | |
| 2004/0162618 A1 * | 8/2004 | Mujwid et al. | 623/17.15 |
| 2004/0220580 A1 | 11/2004 | Johnson et al. | |
| 2004/0249461 A1 * | 12/2004 | Ferree | 623/17.11 |
| 2005/0107878 A1 * | 5/2005 | Conchy | 623/17.11 |
| 2005/0107880 A1 * | 5/2005 | Shimp et al. | 623/17.11 |
| 2005/0125062 A1 * | 6/2005 | Biedermann et al. | 623/17.11 |
| 2005/0149194 A1 | 7/2005 | Ahlgren | |
| 2005/0283245 A1 * | 12/2005 | Gordon et al. | 623/17.15 |
| 2006/0009845 A1 * | 1/2006 | Chin | 623/17.11 |
| 2006/0069442 A1 * | 3/2006 | Michelson | 623/17.15 |
| 2006/0122701 A1 * | 6/2006 | Kiester | 623/17.11 |
| 2006/0212118 A1 * | 9/2006 | Abernathie | 623/17.11 |
| 2007/0123987 A1 * | 5/2007 | Bernstein | 623/17.11 |
| 2007/0270968 A1 * | 11/2007 | Baynham et al. | 623/17.11 |

FOREIGN PATENT DOCUMENTS

| | | |
|---|---|---|
| FR | 2639823 | 6/1990 |
| FR | 2719763 | 11/1995 |
| WO | 9902214 | 1/1999 |

OTHER PUBLICATIONS

Signus Medical, Tetris, Sep. 2003, 1 page.
Blackstone Medical, Inc., COnstrux PEEK VBR System, 2005, 1 page.
Globus Medical, Sustain R Small (date unknown), 6 pages.
Braddley, S and Cullen J.C., "The Use of Methylmethacrylate in the Treatment of Giant Tumors of the Proximal Tibia", Aust. N.Z. J. Surg. vol. 49, No. 1, Feb. 1979, (3 pgs.).
Campanacci, M., Gui, Rainer, L. and Savini, R., "The Treatment of Tibial Plateau Fractures", Chi. Org. Mov. 72(3), Dec. 1975 (Italian text (pp. 234-256) English translation.
Kyphon Surgical Technique Manual, 1999, (pp. 5,6,9, 16-19).
Kyphon Vertebral Traetment Notebook, date unknown (9 pgs.).
Kyphon web page, www.kyphon.com, Mar. 13, 2001 (1 pg.).
AOM Techniques Manual, date unknown (11 pgs.).

* cited by examiner

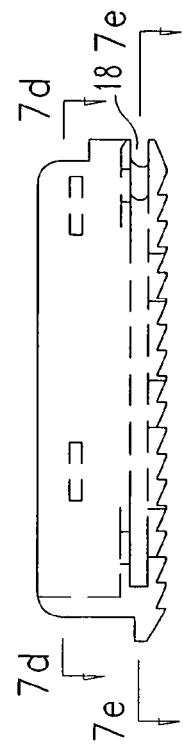
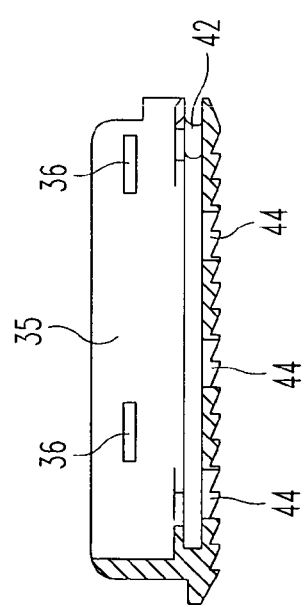
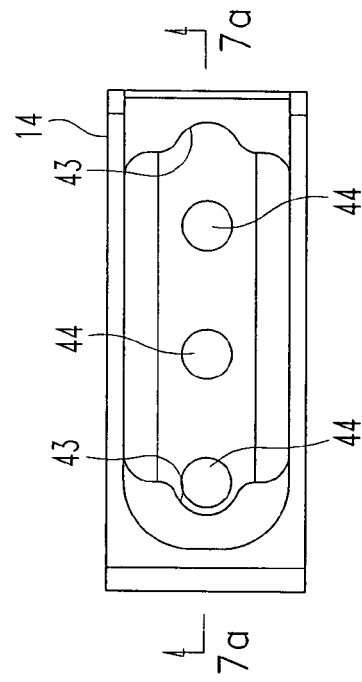
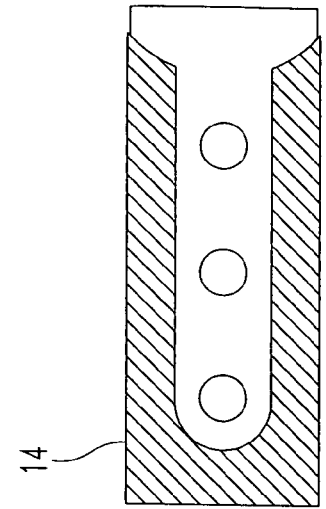
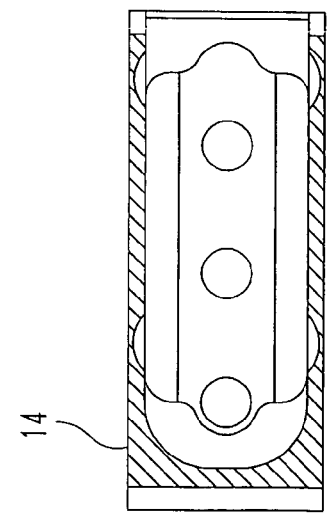

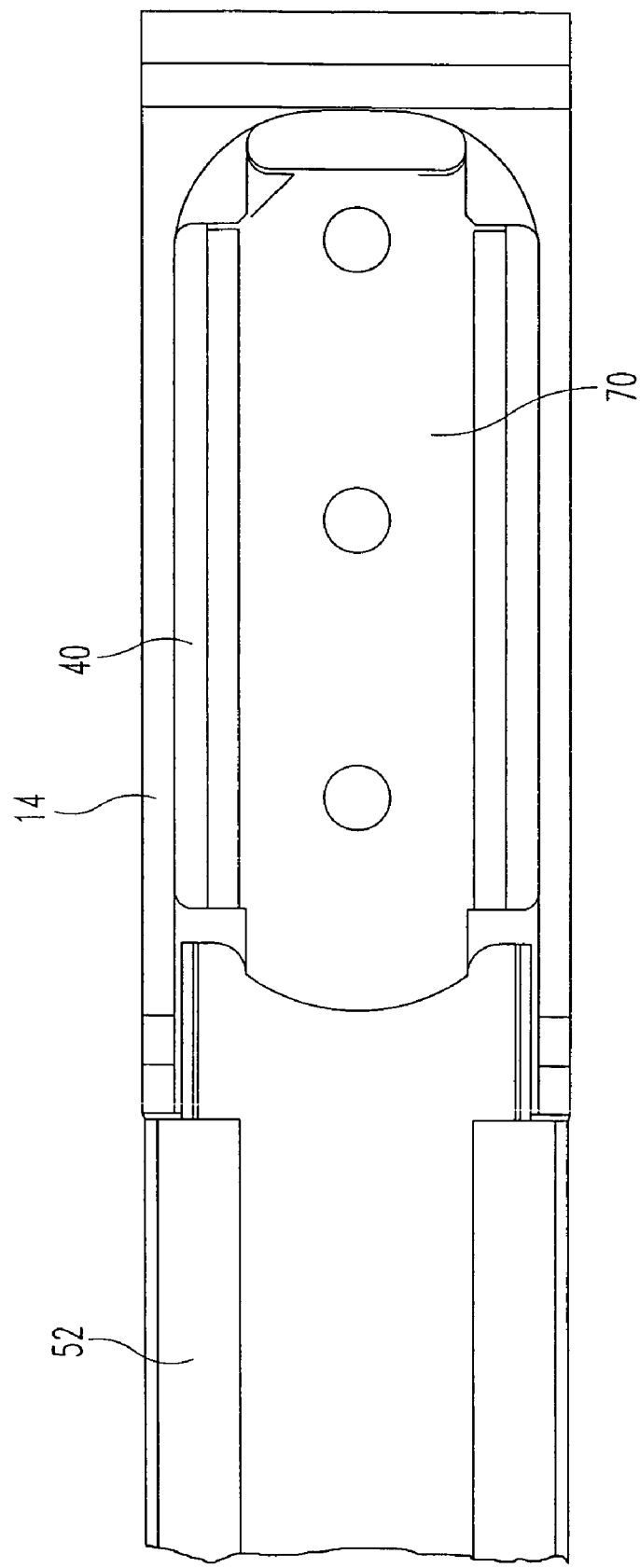

EXPANDABLE INTERBODY FUSION DEVICE

REFERENCE TO RELATED APPLICATION

This application claims priority to co-pending provisional application No. 60/604,422, filed on Aug. 25, 2004, and entitled "Expandable Interbody Fusion Device". The disclosure of this provisional application is incorporated herein by reference.

BACKGROUND OF THE INVENTION

The present invention relates to devices and methods for stabilization of spinal motion segments and most particularly for stabilization of the intervertebral disc space.

The number of spinal surgeries to correct the causes of low back pain has steadily increased over the last several years. Most often, low back pain originates from damage or defects in the spinal disc between adjacent vertebrae. The disc can be herniated or can be suffering from a variety of degenerative conditions, so that in either case the anatomical function of the spinal disc is disrupted. The most prevalent surgical treatment for these types of conditions has been to fuse the two vertebrae surrounding the affected disc. In most cases, the entire disc will be removed, except for the annulus, by way of a discectomy procedure. Since the damaged disc material has been removed, something must be positioned within the intradiscal space, otherwise the space may collapse resulting in damage to the nerves extending along the spinal column.

In order to prevent this disc space collapse, the intra-discal space has been filled with bone or a bone substitute in order to fuse the two adjacent vertebrae together. In early techniques, bone material was simply disposed between the adjacent vertebrae, typically at the posterior aspect of the vertebrae, and the spinal column was stabilized by way of a plate or a rod spanning the affected vertebrae. With this technique once fusion has occurred the hardware used to maintain the stability of the segment became superfluous. Moreover, the surgical procedures necessary to implant a rod or plate to stabilize the level during fusion were frequently lengthy and involved.

It was therefore determined that a more optimum solution to the stabilization of an excised disc space is to fuse the vertebrae between their respective end plates, most optimally without the need for anterior or posterior plating. There have been an extensive number of attempts to develop an acceptable intra-discal implant that could be used to replace a damaged disc and yet maintain the stability of the disc interspace between the adjacent vertebrae, at least until complete arthrodesis is achieved. These "interbody fusion devices" have taken many forms, but many have had difficulty in achieving fusion, at least without the aid of some additional stabilizing device, such as a rod or plate. Moreover, some of these devices are not structurally strong enough to support the heavy loads and bending moments applied at the most frequently fused vertebral levels, namely those in the lower lumbar spine.

The interbody fusion devices (IBFDs) that have overcome these difficulties are typically bulky, at least with respect to the intervertebral space. In particular, these devices have been configured to completely fill the space and to restore the normal spinal anatomy at the instrumented level. One drawback of this approach is that the implant device is not exactly sized to the anatomy of the particular patient, thus typically requiring pre-distraction of opposed vertebrae in order to increase the disc space for device implantation. While a collection of differently sized IBFDs can be provided, it is unwieldy and impractical to provide an IBFD sized for every intervertebral disc space height.

Another drawback of these prior devices is that that the surgical insertion site must be at least as big as the IBFD. Minimally invasive and working channel surgical techniques have been recently developed that have significantly reduced the surgical invasion, but even more improvement is needed. The present invention provides an IBFD that achieves all of the benefits of prior IBFD designs, while also addressing the above-noted drawbacks.

SUMMARY OF THE INVENTION

In order to address these drawbacks, the present invention contemplates an expandable interbody fusion device for implantation into the intradiscal space between two opposing vertebral bodies of a spine which comprises a superior endplate member having an upper surface for engaging a superior vertebral body in a spine and an inferior endplate member having a lower surface for engaging an inferior vertebral body in the spine, the superior endplate member and the inferior endplate member being releasably coupled and defining a cavity therebetween. The device is further provided with at least one expansion member configured to be introduced into the cavity to move the superior endplate and the inferior endplate member relatively apart upon introduction and to thereby decouple the superior endplate member and the inferior endplate member. In one embodiment, the superior endplate member has a pair of opposing spaced apart sidewalls depending downwardly from the upper surface, while the inferior endplate member has a pair of opposing spaced apart sidewalls projecting upwardly from the lower surface. The depending sidewalls of the two endplate members are configured to overlap for an extent as the superior endplate member and the inferior endplate member are moved apart.

In one feature, at least one of the sidewalls on one of the superior endplate member or the inferior endplate member comprises a projecting prong while an overlapping sidewall of the other of the superior endplate member or the inferior endplate member defines a complementary notch for receipt of the prong. The prong and the notch thus form a releasable coupling between the superior endplate member and the inferior endplate member.

In a further embodiment, the superior endplate member has at least one end wall depending downwardly from the upper surface and the inferior endplate member has at least one end wall projecting upwardly from the lower surface. The depending end walls are configured to overlap for an extent as the superior endplate member and the inferior endplate member are moved apart.

In certain embodiments of the invention, the upper surface of the superior endplate member and the lower surface of the inferior endplate member each comprise gripping surfaces for engagement with the respective superior and inferior vertebral bodies. These gripping surfaces may be defined by ribs having a generally saw-toothed configuration. Furthermore, at least one of the upper surface of the superior endplate member or the lower surface of the inferior endplate member may be angled to provide a particular angle between the opposing vertebral bodies. At least one of the upper surface of the superior endplate member or the lower surface of the inferior endplate member may be curved to provide anatomical support of the vertebral bodies.

In accordance with certain features of the invention, the at least one expansion member is a generally flat wafer configured for sliding insertion into the cavity under sufficient pressure to move the superior endplate member and the inferior endplate member apart. The wafer may comprise a surface for cooperative engagement with at least the superior endplate member. Preferably, the device comprises a plurality of wafers slidably received in contact to form a stack of wafers within the cavity and to separate the superior plate from the inferior plate when the height of the stack exceeds the size of the cavity in the device.

In one specific embodiment, each of the wafers has an upper generally flat surface and a lower generally flat surface. In another specific embodiment, a lower flat surface of a wafer in the stack and an upper flat surface of a contacting wafer comprise complementary interdigitating configurations to provide at least lateral and rotational stability to the stack of wafers. These complementary configurations may be defined by a ridge on at least one of the wafer surfaces and a trough for receiving the ridge on a surface of a contacting wafer.

In a further embodiment of the invention, an expandable interbody fusion device is provided for implantation into the intradiscal space between two opposing vertebral bodies of a spine, in which the device comprises a superior endplate member having an upper surface for engaging a superior vertebral body in a spine and an inferior endplate member having a lower surface for engaging an inferior vertebral body in the spine, the superior endplate member and the inferior endplate member defining a cavity therebetween. The device further comprises at least one expansion member configured to be introduced into the cavity and upon introduction to move the superior endplate member and the inferior endplate member relatively apart. The superior endplate member and the inferior endplate member define cooperative surfaces that overlap for an extent as the superior endplate member and the inferior endplate member move apart to thereby provide stability to the device upon expansion.

In accordance with other features of the invention, an apparatus is provided for use in restoring the anatomical height of a damaged or diseased disc space between two opposing vertebral bodies in a spine. The apparatus comprises an expandable interbody fusion device according to embodiments described above, together with an inserter releasably connected to the fusion device. The inserter may comprise a track along which the expansion element is conveyed for introduction into the cavity of the fusion device. In one aspect, a separable interface is provided between the track and the fusion device. That interface may be a connector plate supported by the inferior endplate member. The connector plate includes a support surface on one side for supporting the expansion member and at least one severable member on the other side for temporarily holding the track to the fusion device. The connector plate may interface with a movable release plate supported by the track and having a cutting surface operable upon movement to sever the at least one severable member on the connector plate, to thereby allow removal of the track from the fusion device.

An expandable interbody fusion device for implantation into the intradiscal space between two opposing vertebral bodies of a spine comprises a curved superior endplate member and a curved inferior endplate member, wherein at least one of the superior endplate member or the inferior endplate member has a thickness at one side different from the thickness at the opposite side, thereby defining a lordotic angle between opposing vertebral bodies. A plurality of wafers may be stacked between the superior endplate member and the inferior endplate member, the wafers each being of relatively constant thickness from one side to the other. In certain embodiments, both the superior endplate member and the inferior endplate member have a thickness on one side different from the thickness on the other side.

In one feature, the device defines cooperative interlocking surfaces between the wafers. Cooperative interlocking surfaces may also be defined between the wafers and the superior and inferior endplate members. The cooperative interlocking surfaces may constitute dovetail configurations.

Additional embodiments of the invention reside in an expandable interbody fusion device for implantation into the intradiscal space between two opposing vertebral bodies of a spine that comprises a superior endplate member, an inferior endplate member, and a plurality of wafers stacked between the superior endplate member and the inferior endplate member, wherein each of the wafers has a different thickness from side to side to thereby provide upon disposition between the superior endplate member and the inferior endplate member a lordotic angle between the vertebral bodies. Again, the device may define cooperative interlocking surfaces between the wafers, as well as between the wafers and the endplate members.

In a further embodiment, a device is provided for distracting a body tissue space between opposing tissue surfaces which comprises an upper plate having an outer surface configured to contact one of the opposing surfaces and a lower plate having an outer surface configured to contact the other of the opposing surfaces, the lower plate having opposite side walls configured to removably support the upper plate thereon. The upper and lower plates define a cavity when the upper plate is supported on the lower plate. The lower plate defines a wafer support surface for supporting at least one wafer within the cavity, and a channel communicating with the cavity and configured to receive a wafer conveyed therethrough for placement on the surface of the lower plate. In one feature of this embodiment, the upper plate defines a contact surface for contacting a wafer within the cavity to displace the upper plate from the lower plate.

It is one object of the invention to provide an expandable device that may be manipulated percutaneously to distract the space between two tissue surfaces, such as the intervertebral disc space. Another object resides in features of the invention that provides for controlled expansion of superior and inferior plates configured to engage the tissue surfaces.

One benefit of the various embodiments disclosed herein is that all of the components are configured for easy introduction to the surgical site through a working channel cannula and without the need for traditional open surgical procedures. Another benefit is that the overall height of the expandable device, and thus the amount of distraction applied to the tissue surfaces, may be easily controlled during the distraction procedure. Other objects and benefits of the invention will become apparent from the following written description and accompanying figures.

DESCRIPTION OF THE FIGURES

FIGS. 7a-7e include side, top and cross-sectional views of the inferior endplate portion of the IBFD shown in FIGS. 6a-6e.

FIGS. 14a-c are top, top perspective and top-perspective cut-away views of components of the insertion apparatus engaged with the inferior endplate portion of the IBFD illustrated in FIGS. 6-7 and including the distal end of the wafer track shown in FIG. 13.

DESCRIPTION OF THE PREFERRED EMBODIMENTS

Figure 1:
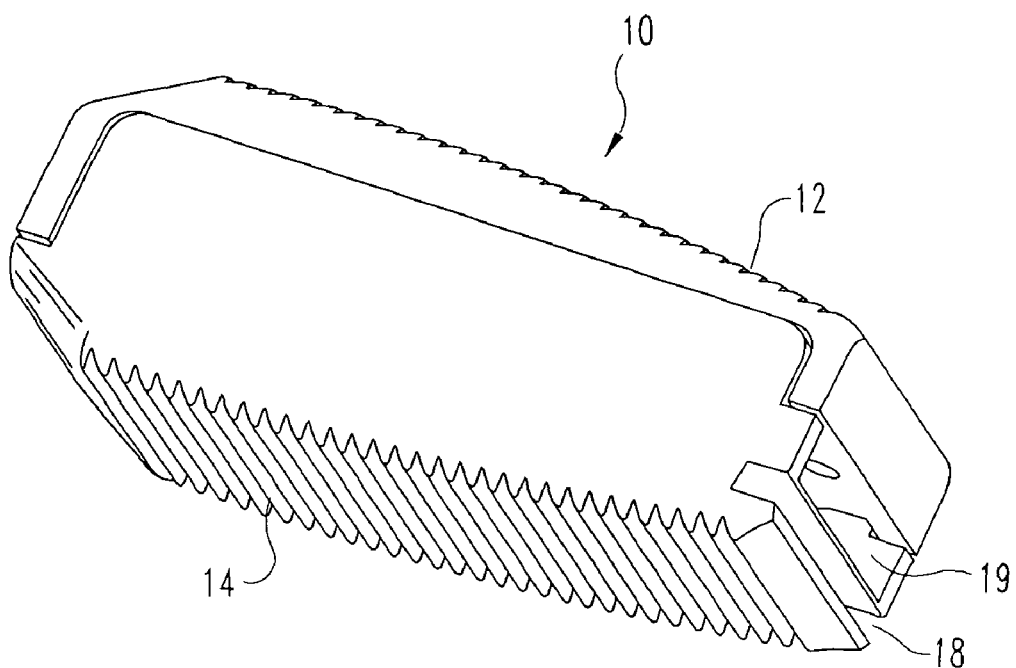
FIG. 1 is a bottom perspective view of an interbody fusion device (IBFD) according to one embodiment of the invention.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 2:
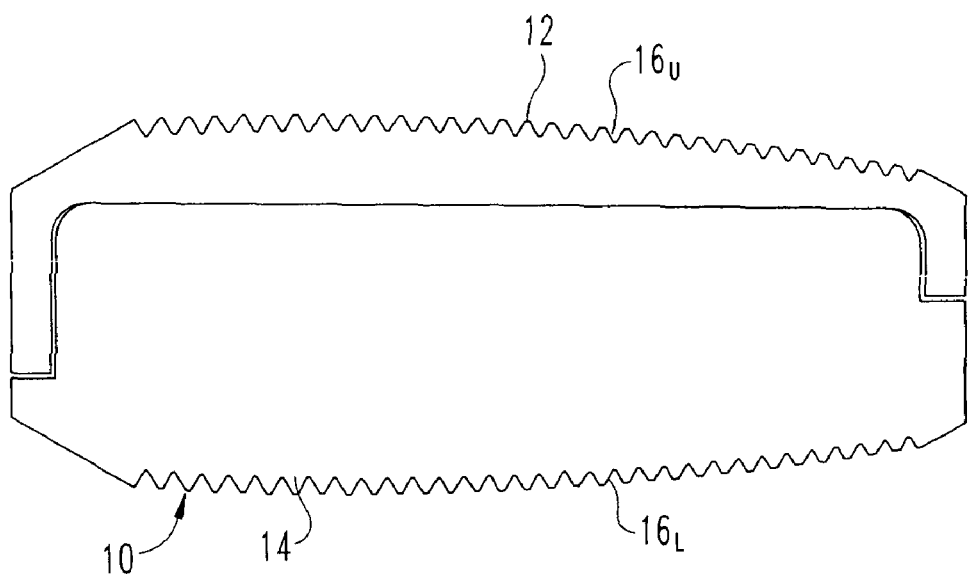
FIG. 2 is a side view of the IBFD shown in FIG. 1.

In accordance with one embodiment of the invention, an interbody fusion device (IBFD) 10 includes a superior endplate 12 and an inferior endplate 14 that define a wafer cavity 19, as shown in FIGS. 1-2. The superior and inferior surfaces of the endplates define engagement ribs $16_U$ and $16_L$ that are configured to engage or grip the vertebral endplates of opposed vertebrae in a spine. Preferably, the ribs $16_U$ and $16_L$ are configured to prevent expulsion of the IBFD under normal spinal loads. For instance, the ribs may have a saw tooth shape that is inclined toward the opening through which the IBFD is inserted into the interbody space. Angling the ribs toward the opening also angles them away from the direction of insertion so that the IBFD can be easily inserted into a collapsed space.

Figure 3:
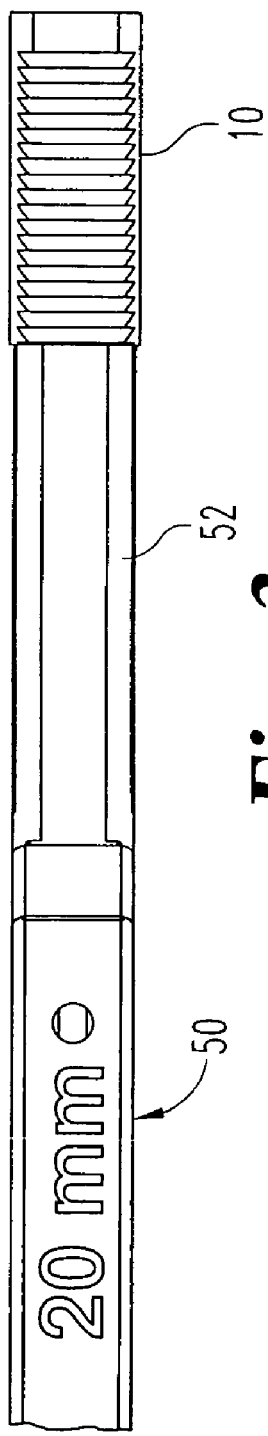
FIG. 3 is a top view of the IBFD of FIGS. 1-2 mounted on an insertion apparatus in accordance with one aspect of the invention.
Figure 4:
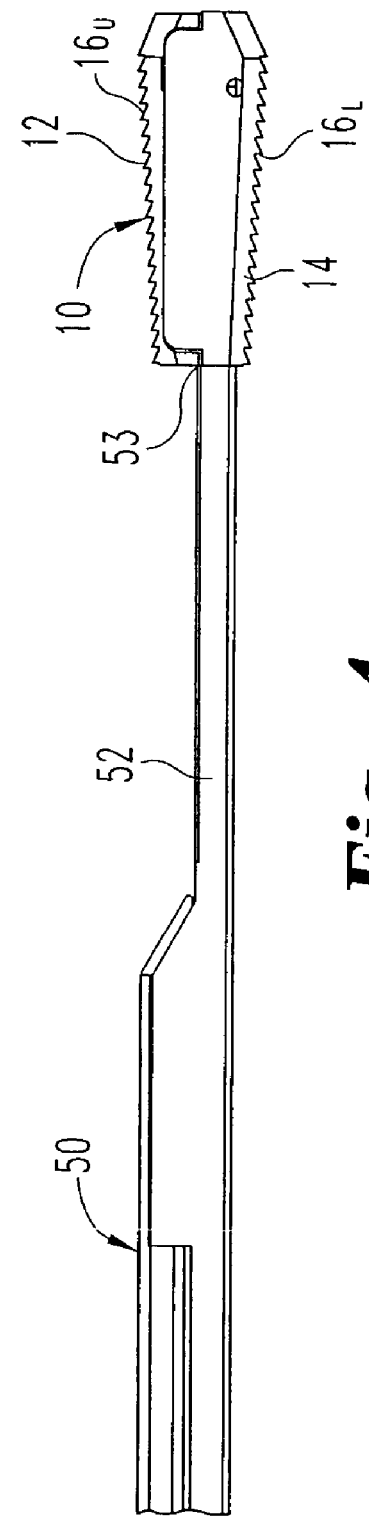
FIG. 4 is a side view of the IBFD and insertion apparatus shown in FIG. 3.
Figure 5A:
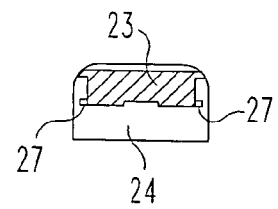
FIGS. 5a-5f include perspective, side, end, top and bottom views of a superior endplate portion of the IBFD shown in FIGS. 1-2, and including a cross-sectional and enlarged view of portions thereof.
Figure 5B:
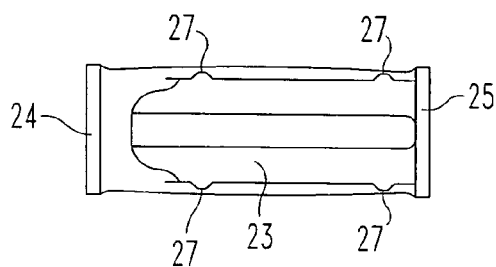
Figure 5C:
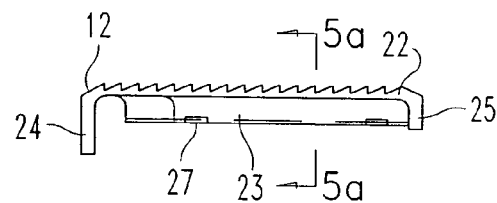
Figure 5D:
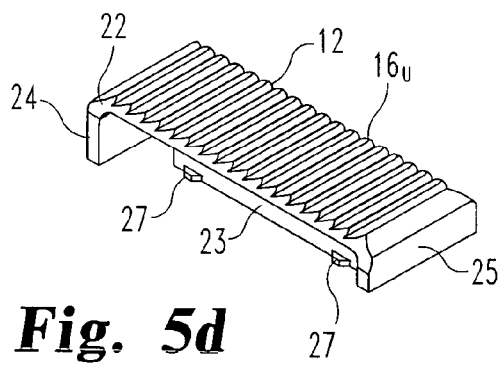
Figure 5E:
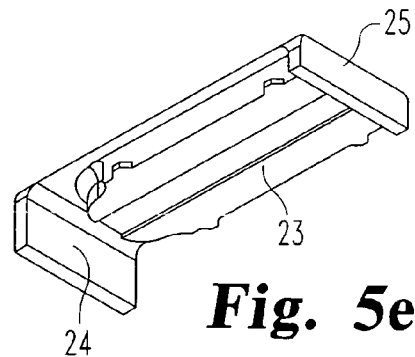
Figure 5F:
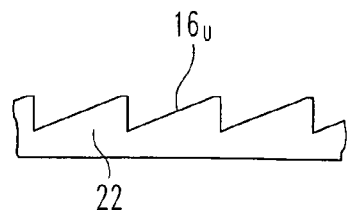
Figure 6A:
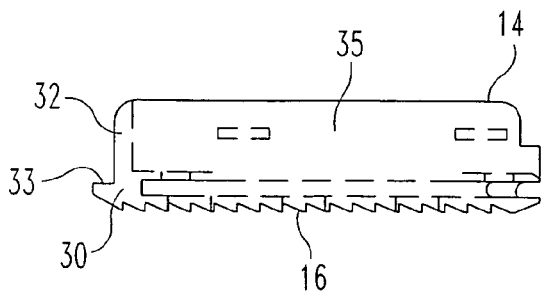
FIGS. 6a-6e include perspective, side, end, top and bottom views of an inferior endplate portion of the IBFD shown in FIGS. 1-2, including an enlarged view of a portion thereof.
Figure 6B:
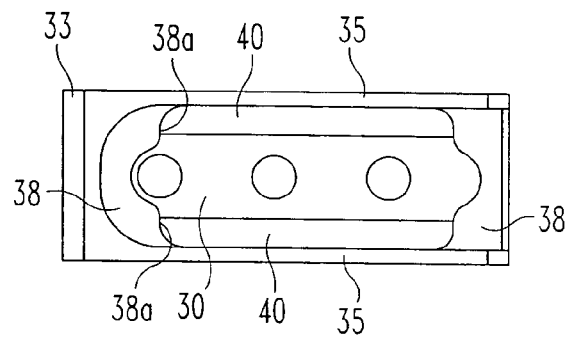
Figure 6C:
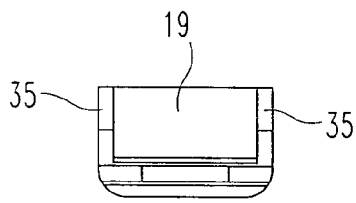
Figure 6D:
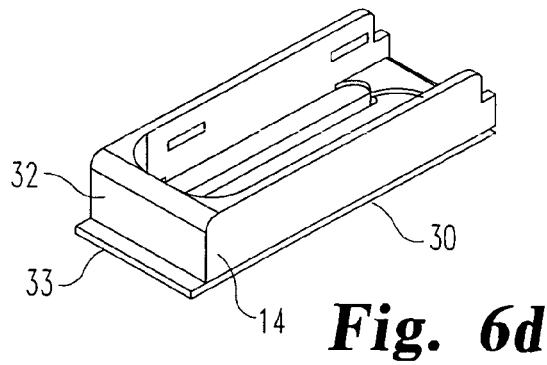
Figure 6E:
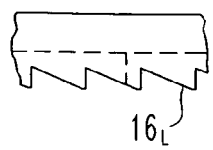

The IBFD 10 also defines an inserter cavity 18 that engages a portion of an inserter apparatus 50, as shown in FIGS. 3-4. The inserter apparatus 50 defines a wafer track 52 along which a plurality of expansion members, or wafers, are conveyed to fill the wafer cavity 19.

In accordance with one aspect of the invention, the IBFD 10 has a height across the superior and inferior endplates 12, 14 that is less than the normal anatomic height of a typical intervertebral disc space. The invention contemplates that a series of expansion members, such as wafers, are introduced into the wafer cavity 19 to at least fill all or part of the cavity, and to distract the opposing vertebrae, separating the superior and inferior endplates. Insertion of the wafers separates the endplates to expand the height of the IBFD within the intervertebral or interbody space and to ultimately restore the normal anatomic height of the instrumented disc space.

Details of the superior and inferior endplates can be seen in FIGS. 5-7. Referring to FIGS. 5a-5f, and in particular to FIG. 5d, the superior endplate 12 includes an upper wall 22 on which the engagement ribs $16_U$ are defined. The interior face of the upper wall is thickened in a reinforcement region 23.

This region helps maintain the integrity of the superior endplate 12 and provides a strong surface against which a lifting force can be applied by successive insertion of the wafer. Region 23 is also configured to contain and to cooperate with the wafers, as described below, to provide lateral and torsional stability to the wafer stack.

Figure 9:
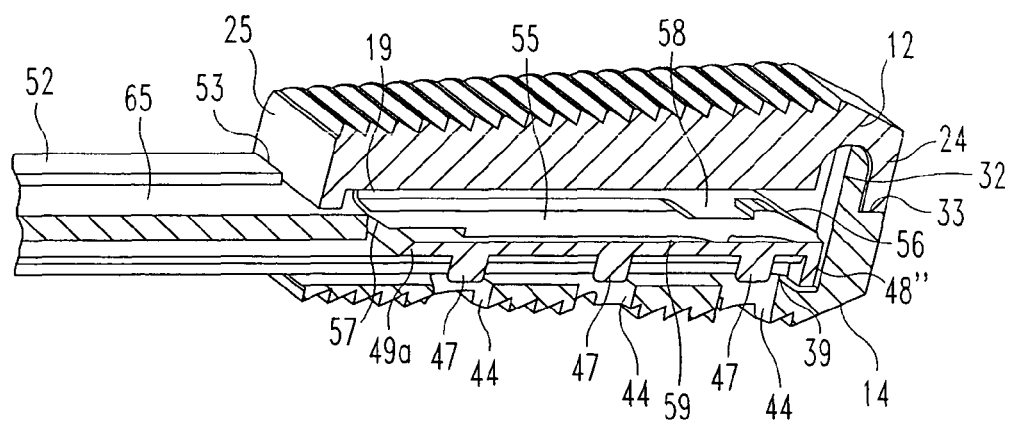
FIG. 9 is a side perspective partial cut-away view of the IBFD and insertion apparatus shown in FIGS. 3-4 with the track connector shown in FIG. 8b in accordance with one embodiment of the invention.

The upper wall terminates in an anatomically anterior end wall 24 and an anatomically posterior end wall 25 that integrate with the inferior endplate 14 as described below. In addition, the reinforcement region 23 defines outwardly and laterally projecting prongs 27 that engage cooperating notches 36 defined in the interior of the inferior endplate 14. Details of the inferior endplate are shown in FIGS. 6-7. The endplate 14 includes a bottom wall 30 on which the engagement ribs $16_L$ are defined. The bottom wall 30 terminates in an end wall 32 and a ledge 33. As shown in FIGS. 2 and 9, the anterior end wall 24 of the superior endplate 12 overlaps the end wall 32 and end ledge 33 when the endplates are initially assembled. The two end walls 24 and 30 overlap over the majority of the height of the end wall 32 so that as the superior and inferior endplates are pushed apart the two endplates remain in contact and continue to define the wafer cavity 19, providing stability to the IBFD as it expands.

The inferior endplate 14 also includes side walls 35 that define the wafer cavity and ultimately help retain the wafers within the cavity as they are sequentially inserted. The inner face of the side walls define notches 36 that are aligned for engagement by the prongs 27 in the superior endplate 12. Thus, when the IBFD is initially assembled prior to insertion into the interbody space, the prongs and notches 27, 36 hold the two endplates together. The interface between the prongs and notches is adequate to hold the IBFD together as it is inserted into the space, but is sufficiently weak to be dislodged under pressure from the inserted wafers.

The interior of the inferior endplate 14 includes opposite surfaces 38 that structurally reinforce the IBFD under large compressive loads. Slightly offset from the walls 38 are support rails 40 (FIG. 6b) that support the track connector 46 shown in FIGS. 8a-8f. The top surface 49 of the track connector 46 is configured to be superior to surface 38 such that any compressive load from the wafer stack is transmitted through the bottom surface of the track connector to the support rails 40. The end walls 38 of the endplate 14 also form end notches 43 (FIG. 7c) that are complementary to the end edges of the track connector 46 in one embodiment of the invention. The end walls 38 and rails 40 of the endplate 14 define a connector channel 42, as shown in FIG. 7a, which is configured to receive the distal end of the wafer track of inserter apparatus 50, as described below.

The superior and inferior endplates 12, 14 can be formed of a biocompatible material with sufficient strength to support the adjacent vertebrae without fatigue and fracture. Preferably, the two endplates are molded from a biocompatible polymeric material, such as, for example, PEEK or a biocompatible composite material, such as, for example carbon-fiber-reinforced PEEK. The material may also be selected to permit tissue ingrowth to integrate with the vertebral endplates. The endplates can further be formed from a moldable or formable biologic material, such as bone.

In accordance with one aspect of this invention, the IBFD 10 is configured to be introduced into the interbody space by an introducer or inserter apparatus 50. The inserter can be constructed and operated like the insertion apparatus disclosed in U.S. Pat. No. 6,595,998, entitled "Tissue Distraction Device", which issued on Jul. 22, 2003, to the assignee of the present invention. The disclosure of this patent, and particularly its discussion of the wafer inserter, is incorporated herein by reference. Alternatively, the inserter can be constructed and operated like the insertion apparatus disclosed in co-pending application Ser. No. 10/813,819, entitled "Tissue Distraction Device", filed on May 31, 2004, and assigned to the assignee of the present invention. The disclosure of this co-pending application is incorporated herein by reference.

For purposes of illustration, certain details of the inserter 50 will be explained herein. As shown in FIG. 3, the apparatus includes a wafer track 52 along which wafers are conveyed to fill the wafer cavity 19 within the IBFD and ultimately to expand the height of the IBFD. Once the last wafer has been introduced into the IBFD it is necessary to remove the inserter 50. The preferred embodiment of the invention contemplates a track connector 46 that helps to integrate the wafer track 52 with the interior cavity of the IBFD and to provide a support surface for the wafer stack within the IBFD.

Details of the track connector 46 are shown in FIGS. 8a-8f and FIG. 9. In particular, the connector 46 includes connector posts 47 that project downward with the IBFD, as best seen in FIG. 9. These posts engage corresponding openings 71 in an insertion plate 70 (see FIG. 12) to provide an interface between the inserter apparatus 50 and the IBFD. In one embodiment, the track connector 46 defines interface edges 48 at its opposite ends that are configured to conform to wall 38 in the inferior endplate 14 (see FIG. 6b). The track connector may also include end edges 46a flanking the interface edges that contact wall edges 38a of the endplate 14 to limit the movement of the track connector into the endplate. The track support includes a ramp 49a that helps direct incoming wafers upward from the wafer track 52 to the wafer support surface 49 within the IBFD.

Figure 8A:
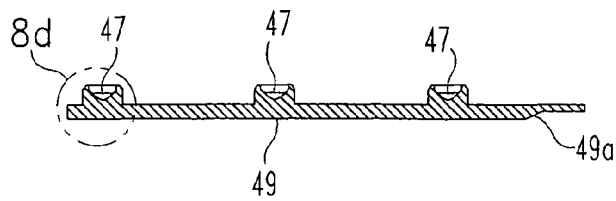
FIGS. 8a-8f include side, top, bottom and perspective views of a track connector used in connection with the insertion apparatus shown in FIGS. 3-4, including cross-sectional views of portions thereof.
Figure 8C:
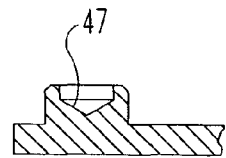
Figure 8B:
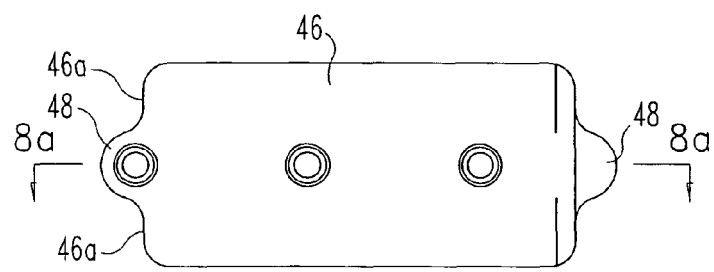
Figure 8D:
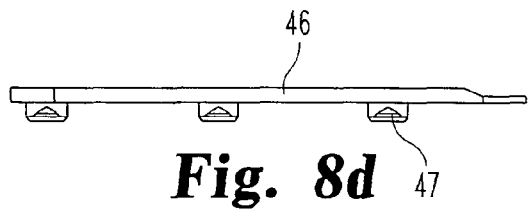
Figure 8E:
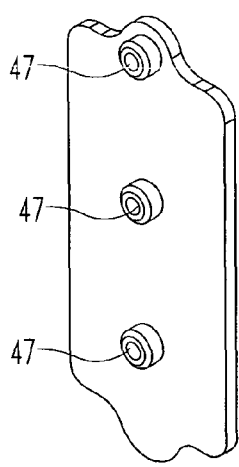
Figure 8F:
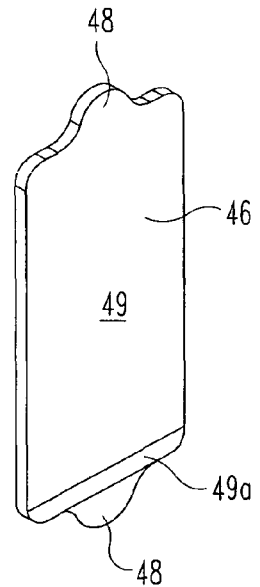
Figure 8G:
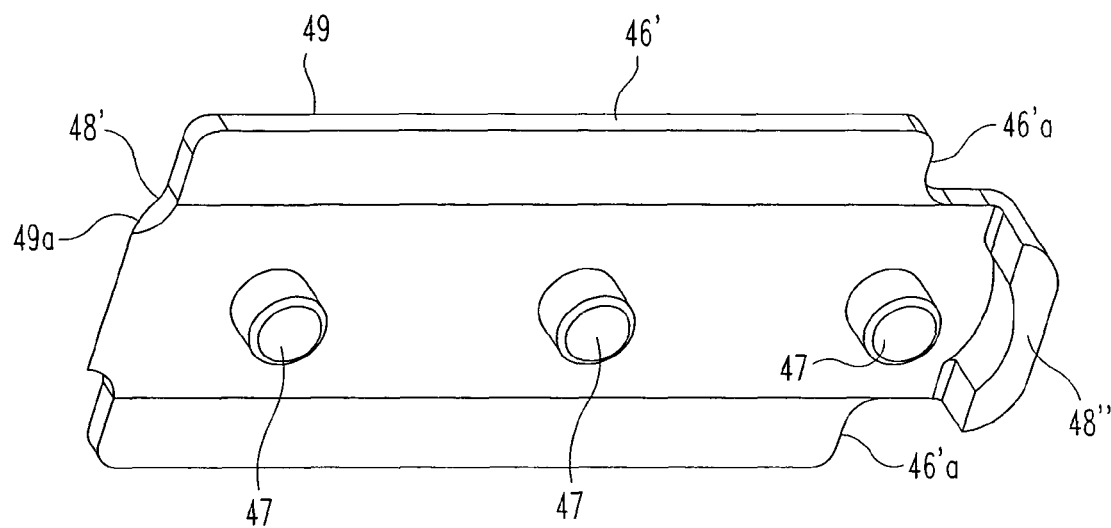
FIG. 8g is a bottom perspective view of an alternative embodiment of a track connector used in connection with the insertion apparatus shown in FIGS. 3-4.
Figure 12:
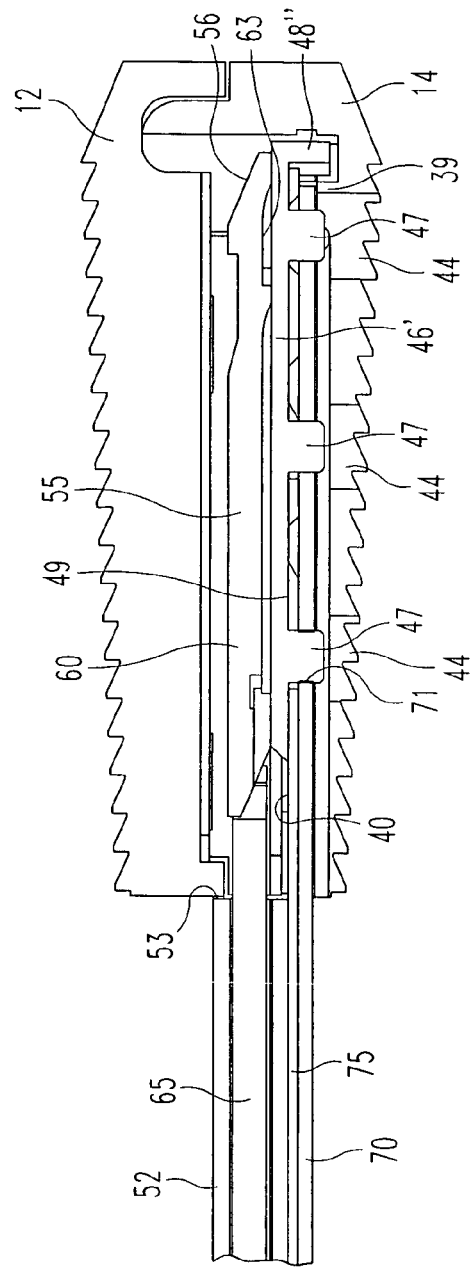
FIG. 12 is a side cut-away view of the structure shown in FIG. 9.
Figure 16A:
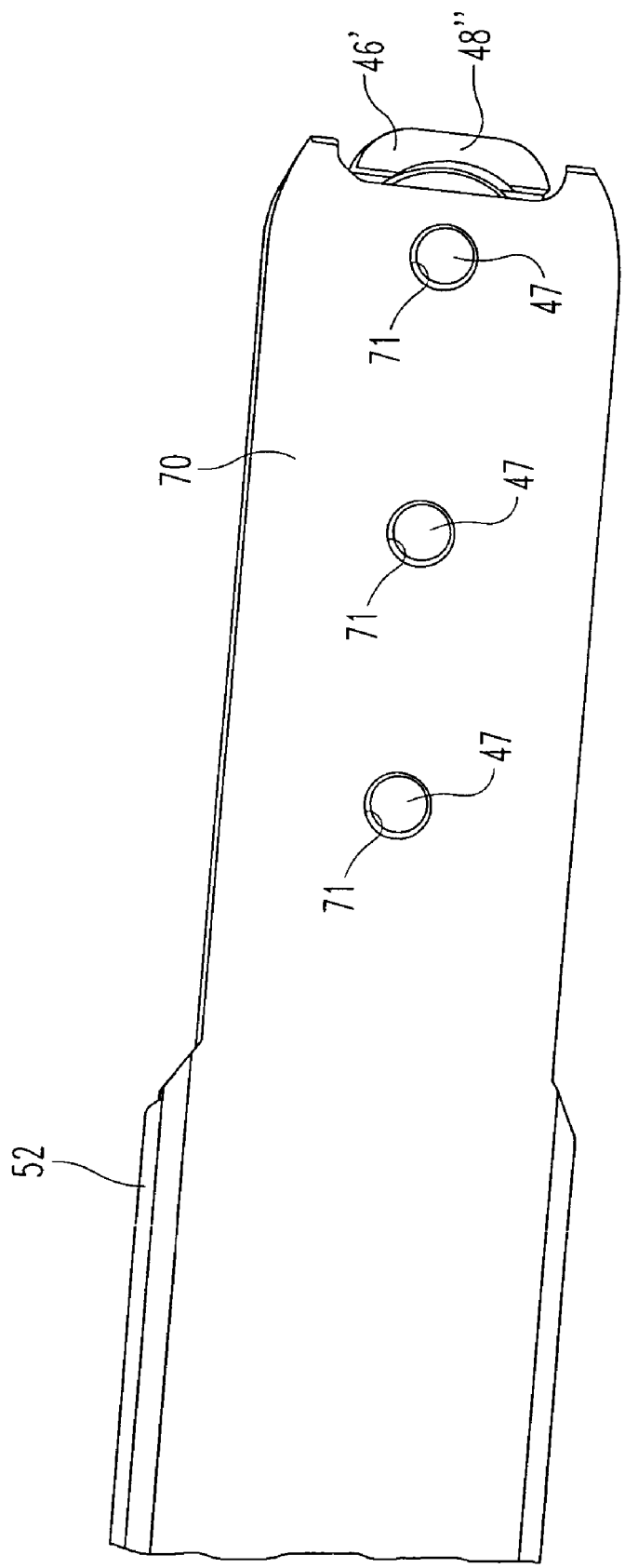
FIG. 16a is a bottom perspective view of the distal end of the wafer track of FIG. 13 with the track connector of FIGS. 8a, 8b mounted thereon.
Figure 16B:
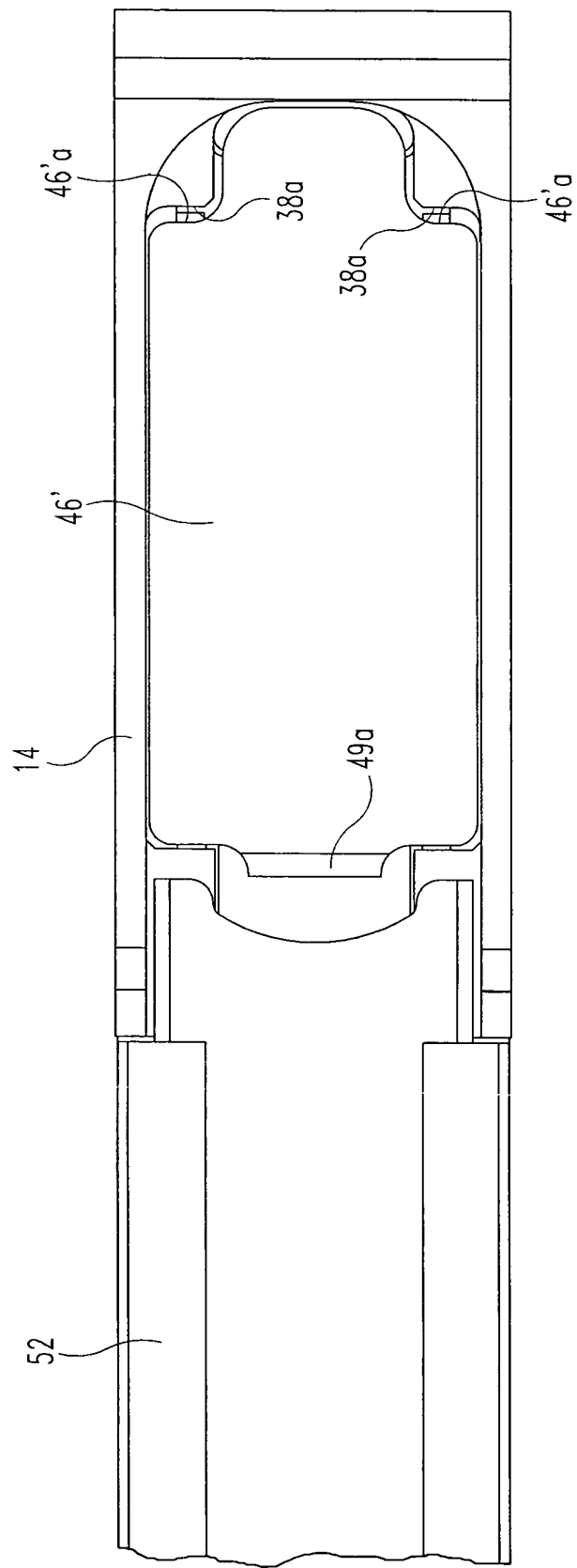
FIGS. 16b-d are top, top perspective and top perspective cut-away views of components of the insertion apparatus engaged with the inferior endplate portion and including the track connector of FIG. 8b prior to wafer insertion.
Figure 16C:
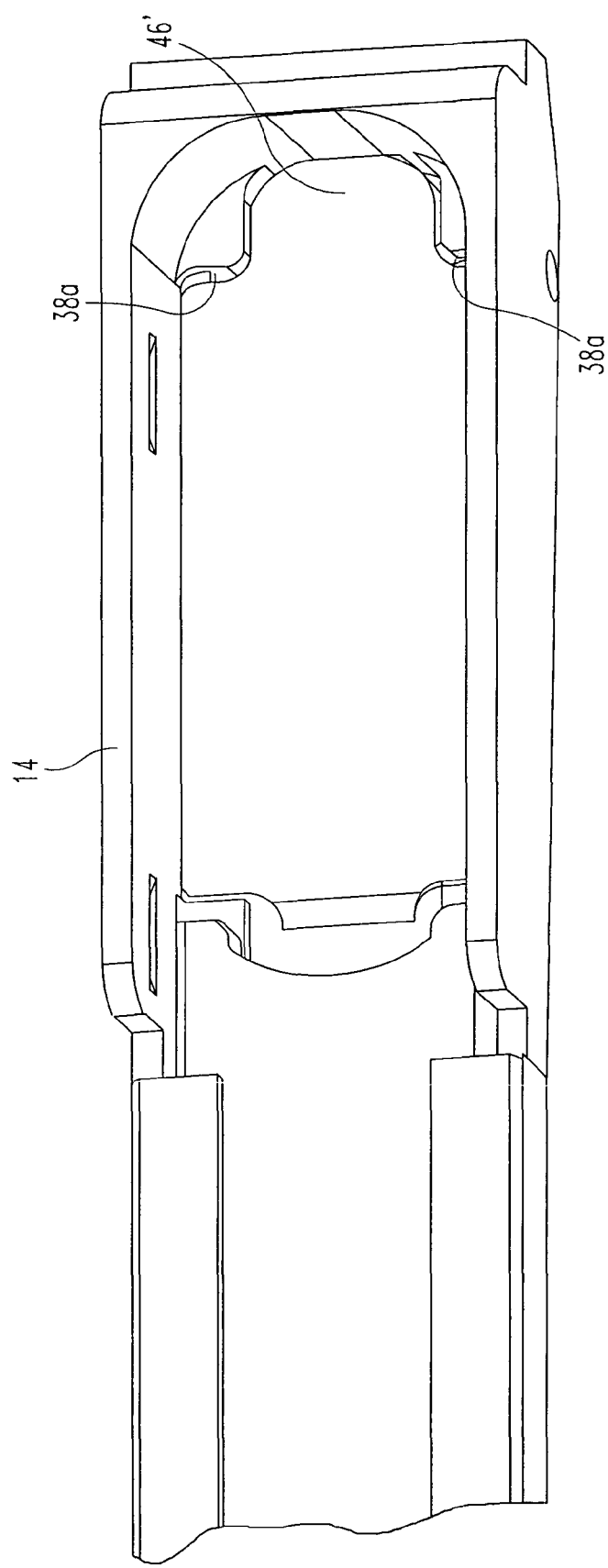

In an alternative embodiment shown in FIG. 8g, a track connector 46' includes a modified proximal end 48' and distal end 48", but still retains the connector posts 47, wafer support surface 49 and ramp 49a. The modified distal end 48" catches against a lip 39 formed in the inferior endplate, as shown in FIGS. 9, 12 to prevent removal of the track connector 46' once it is positioned with the assembled IBFD. The distal end of the track connector 46' further defines end edges 46'a that contact the wall edges 38a, as depicted in FIG. 16b, in the same manner as the end edges 46a described above.

Figure 10:
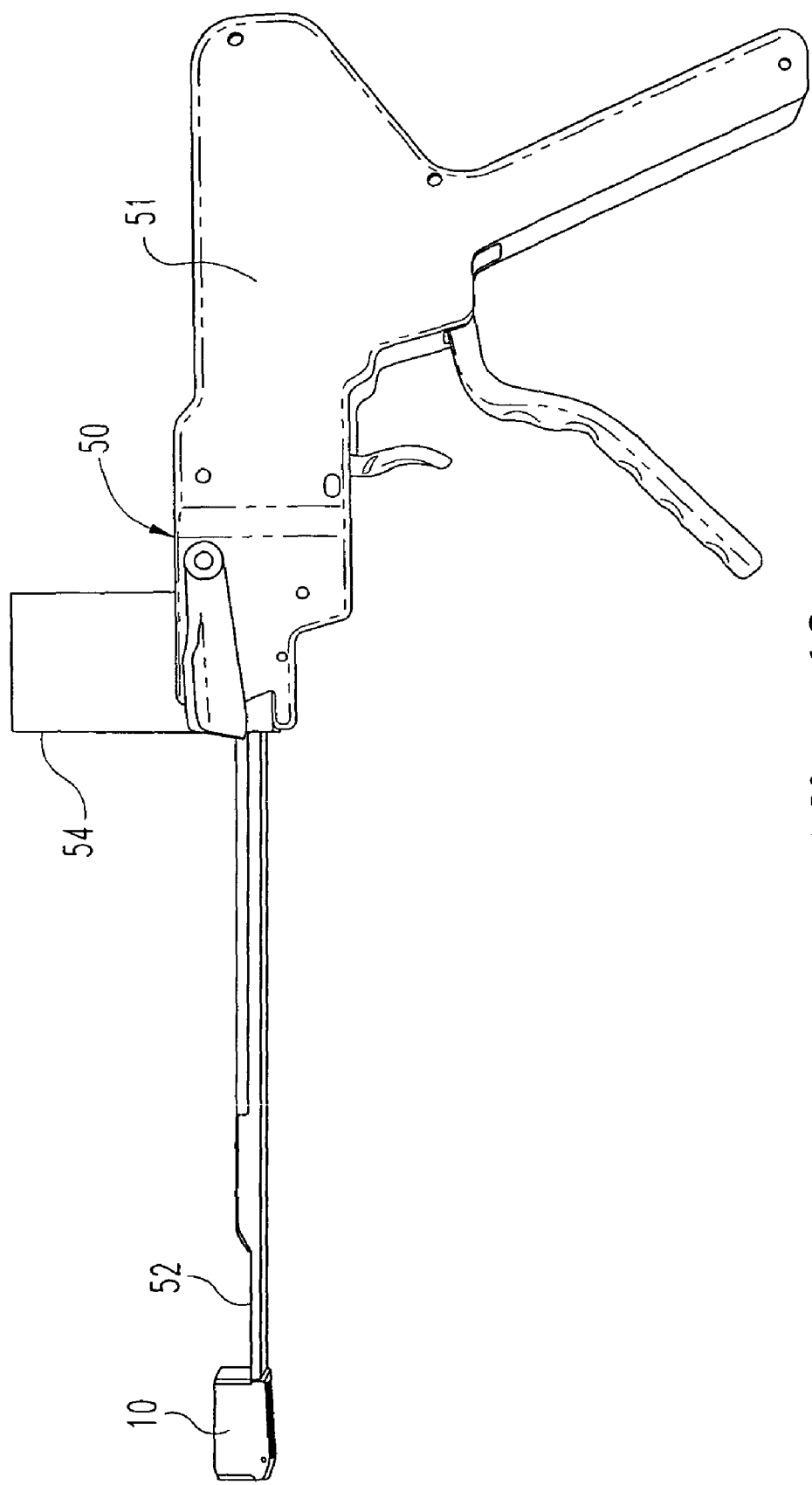
FIG. 10 is a side view of the IBFD and insertion apparatus shown in FIGS. 3-4.
Figure 11A:
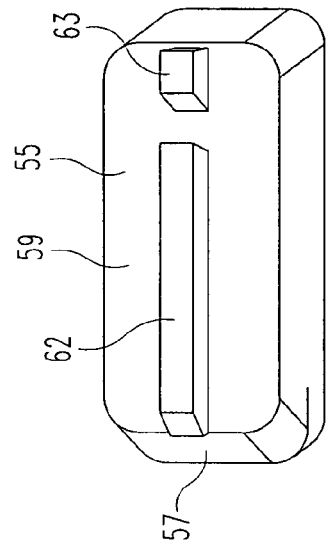
FIGS. 11a, 11b are top perspective and bottom views of a wafer for introduction into the IBFD of FIGS. 1-2 using the insertion apparatus as shown in FIGS. 3-4 and 9.
Figure 11B:
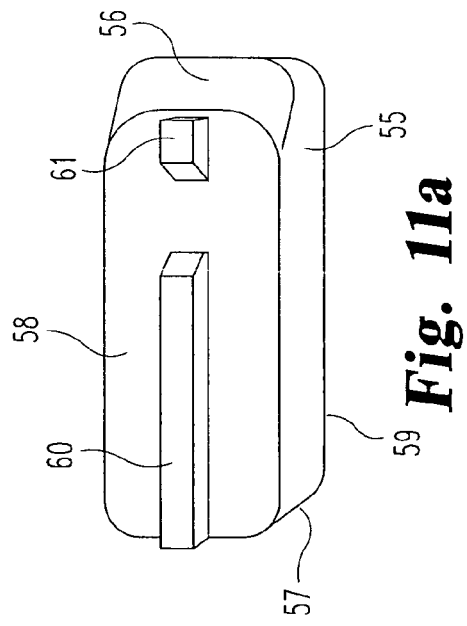

As shown in FIGS. 9, 10 and 12, the wafer inserter apparatus 50 provides an avenue for passage of wafers 55 from a wafer cartridge 54 into the IBFD. The inserter apparatus includes a cartridge gun that extracts wafers 55 consecutively from a stack within the cartridge 54 and conveys them along the track 52 to the IBFD. As shown in FIGS. 11a-b, the wafers 55 are configured for transition along the track 52 and for interlocking engagement within the IBFD. In particular, the wafers include a leading bevel 56 and an opposite trailing bevel 57 to facilitate movement of each successive wafer underneath the immediately prior inserted wafer. The bevels 56, 57 help the incoming wafer dislodge and slide underneath the wafer stack already resident within the IBFD. In certain embodiments, a wafer driver 65 may be provided within the wafer track 52 to advance each wafer into the wafer cavity. The driver 65 can also help hold the lowermost wafer of the stack in position as the inserter apparatus 50 is removed.

The wafers 55 also include interdigitating upper and lower surfaces 58, 59, respectively. The surfaces can assume a variety of configurations intended to prevent relative longitudinal movement between wafers in the stack as well as for lateral and rotational stability. The wafers 55 and their respective surfaces can be constructed as disclosed in U.S. Pat. No. 6,595,998 cited above. The disclosure of this patent, and most particularly its discussion of the construction of the wafers, is incorporated herein by reference. In the preferred embodiment, the upper surface 58 defines a ridge 60 and spaced rib 61 extending along the longitudinal axis of the wafer. Similarly, the lower surface defines a linear trough 62 that receives the ridge 60, and a notch 63 that receives the rib 61.

The insertion configuration for the IBFD and wafer inserter apparatus is generally depicted in FIG. 12. The wafer track 52 of the inserter apparatus engaged the IBFD with the track end 53 contacting the proximal faces of both the inferior endplate 14 and the superior endplate 12. A wafer 55 is shown resting on the wafer support surface 49 of the track connector 46'. The track connector 46 rests on the support rail 40 (see FIG. 6) with its posts 47 projecting downward toward the post openings 44 in the inferior endplate 14. As shown in the figures, the posts do not necessary extend into the openings 44. Instead, the post openings 44 facilitate the assembly of insertion apparatus to the track connector prior to use.

Figure 14B:
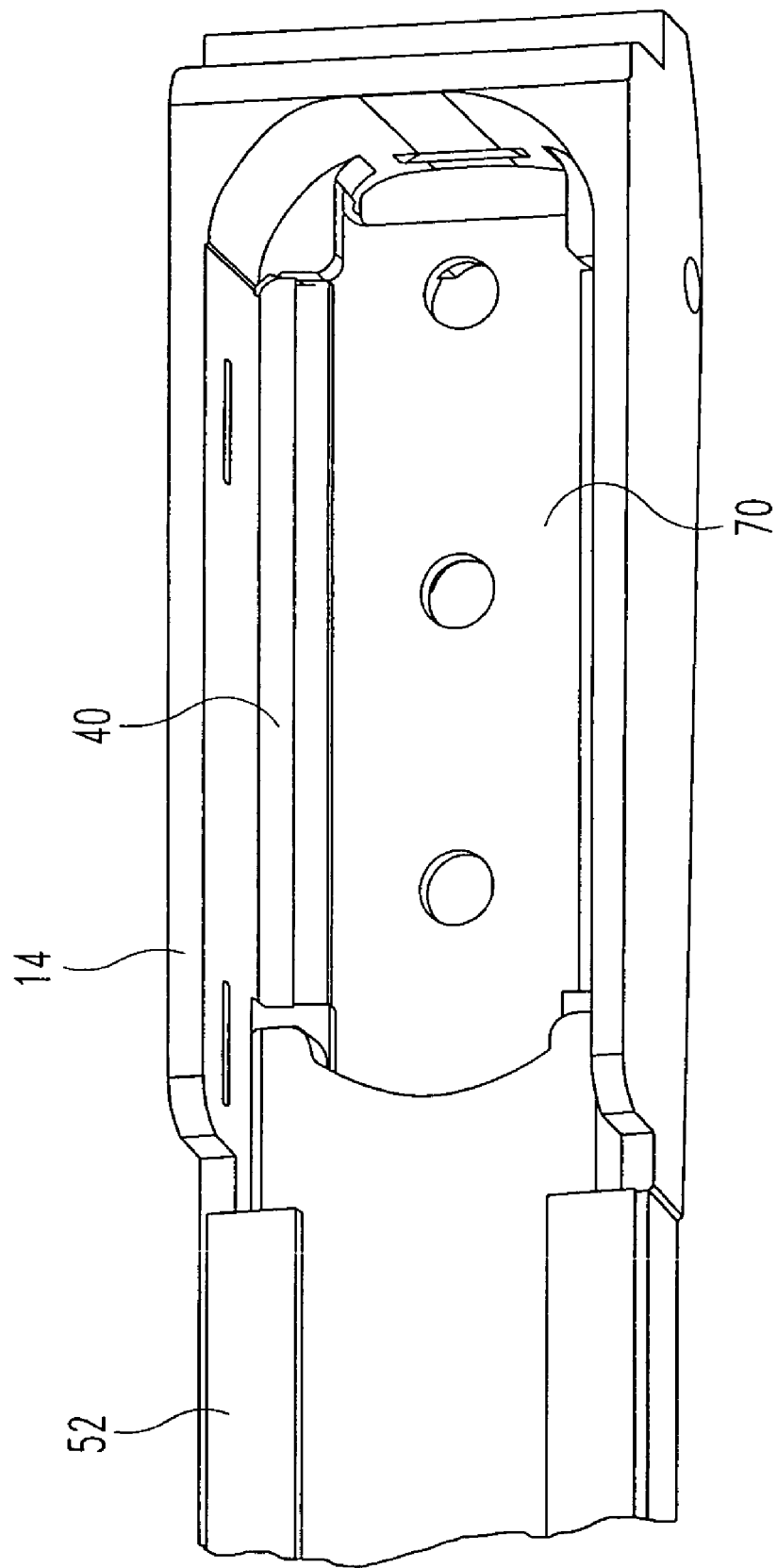
Figure 14C:
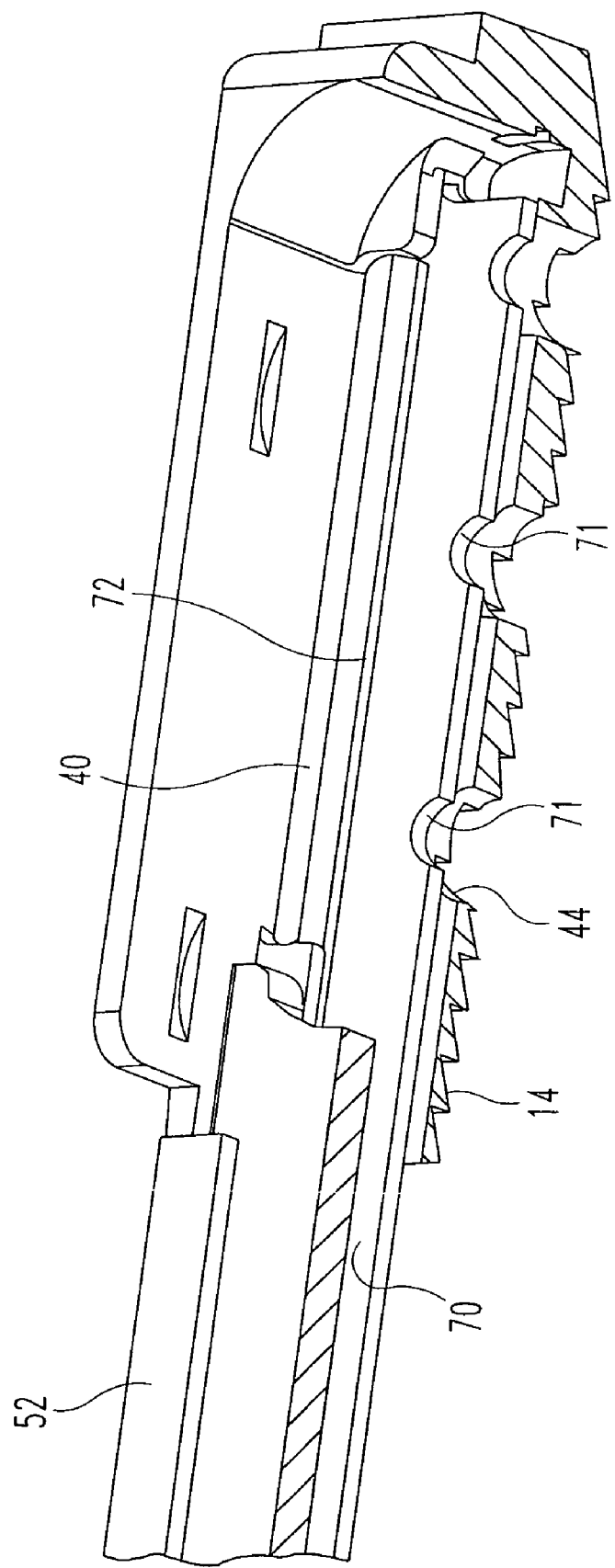

Beneath the track connector 46 reside an insertion plate 70 and a release plate 75 immediately adjacent the connector 46. Both plates provide openings to receive the connector posts 47 therethrough, including openings 71 in the insertion plate and openings 76a-c in the release plate. The insertion plate 70 may define a release track 72 (as shown in FIG. 14c) within which the release plate 75 slides. The release track may be provided to increase the stiffness of the insertion plate, or may be eliminated to permit a reduction in width of the components.

Figure 13:
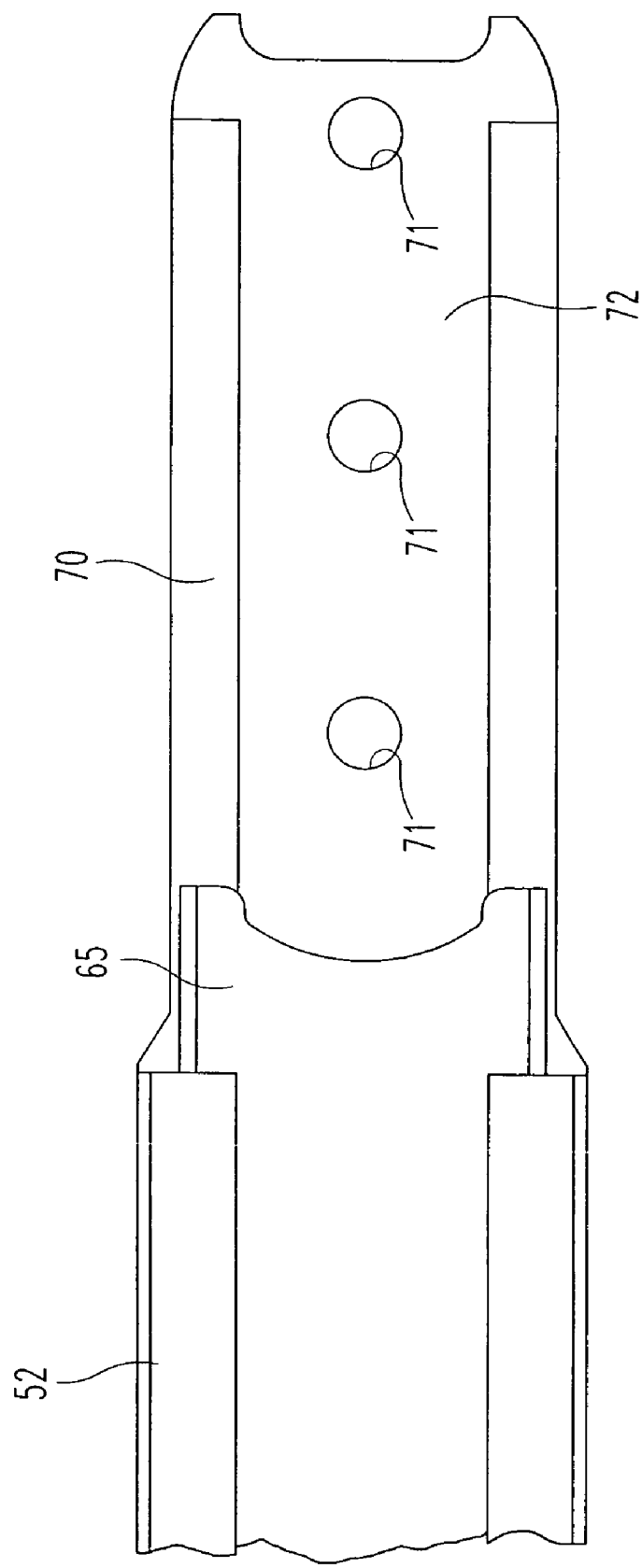
FIG. 13 is a top view of the distal end of the wafer-track portion of the insertion apparatus shown in the prior figures.

The assembly of the components of the inserter apparatus 50 within the IBFD 10 is depicted sequentially in FIGS. 13-18. The insertion plate 70 is shown in FIG. 13. Preferably, the plate 70 is integral with the wafer track 52. As shown in FIG. 12, the insertion plate 70 essentially supports the IBFD with the plate 70 extending into the wafer cavity and the track end 53 abutting the IBFD. This plate 70 will be removed with the inserter apparatus 50, leaving the IBFD within the interbody space. The post openings 71 are sized to receive the connector posts 47 therethrough. As can be seen in FIGS. 14a-c, the insertion plate 70 sits below the support rail 40 in the inferior endplate 14 with its post openings 71 aligned with the post openings 44 in the endplate 14.

Figure 15A:
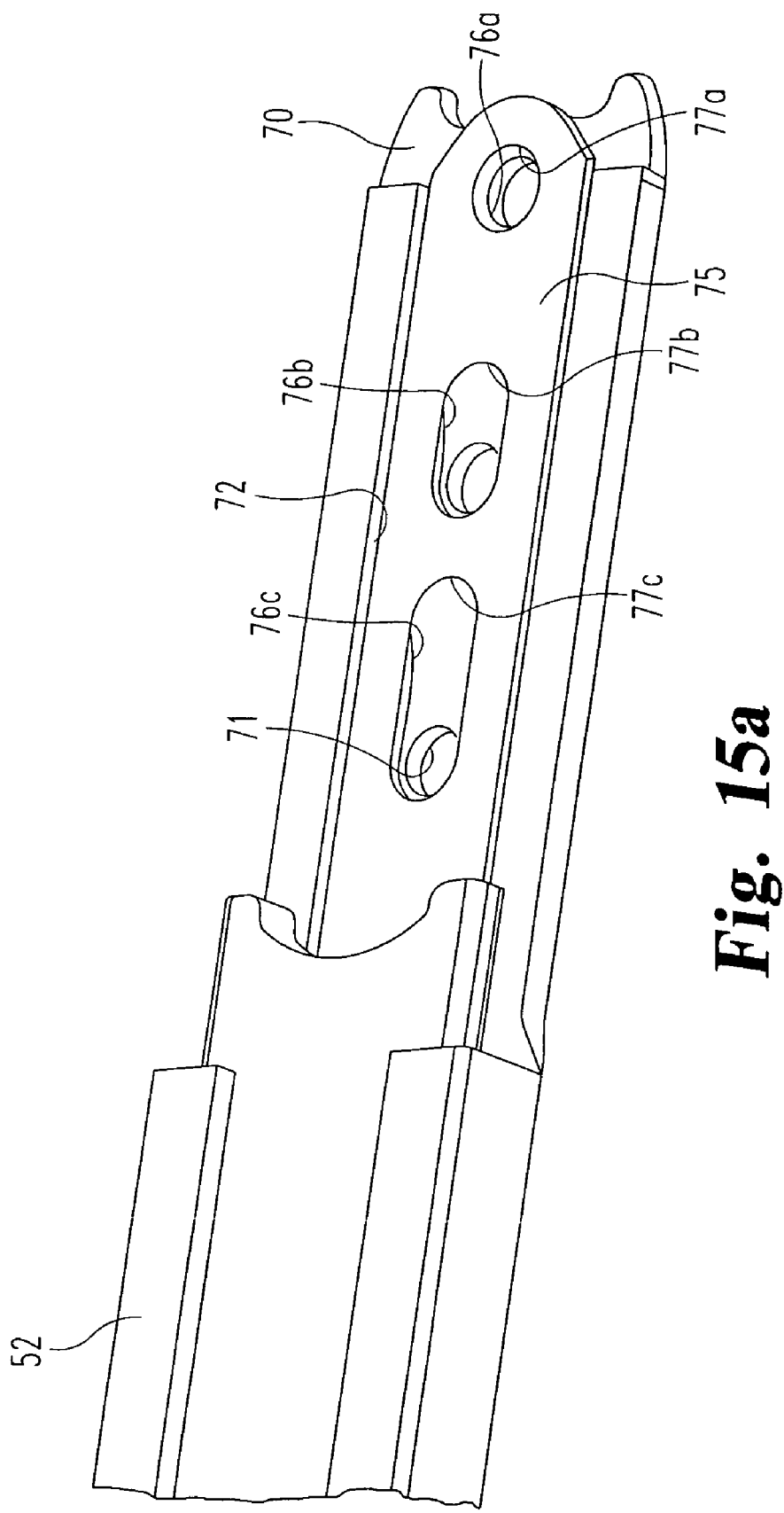
FIG. 15a is a top perspective view of a release plate, driver and the distal end of the wafer track of FIG. 13.
Figure 15B:
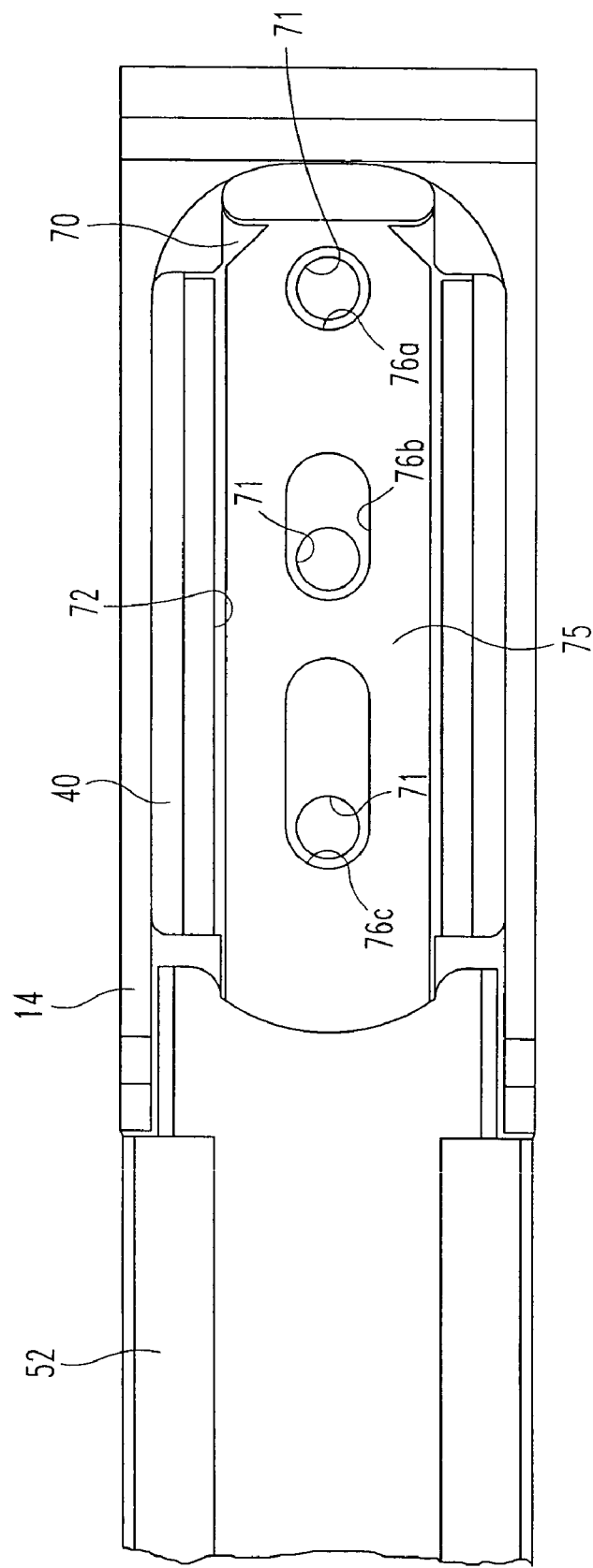
FIG. 15b is a top view of components of the insertion apparatus engaged with the inferior endplate, including the release plate of FIG. 15a. The track connector is removed to show the position of the release plate and the distal end of the wafer track in the inserter cavity.

The release plate 75, as shown in FIGS. 15a-b, is slidably disposed within the release track 72 in the insertion plate 70. In an alternate embodiment, the release plate 75 is slidably disposed on top of the insertion plate 70 without any release track 72. The release plate 75 includes openings 76a-c corresponding to each of the connector posts 47. The distal edge 77a-c of each opening is sharpened so that they will sever the posts 47 from the connector plate 46 when the release plate is pulled proximally, or out of the IBFD. The opening 76a is generally sized slightly larger than the post 47, while the other two openings 76b-c are increasingly elongated. This configuration allows the distal-most post to be cleanly severed before the middle post is severed, and the middle post to be severed before the proximal post. This approach reduces the force needed to sever the posts. Once the posts are severed, they are retained within the post openings 71 via an interference fit, since they are no longer needed to hold the track connector within the IBFD. When the posts are severed, the inserter apparatus 50 can be removed from the implanted IBFD without risk of retracting the IBFD.

Figure 16D:
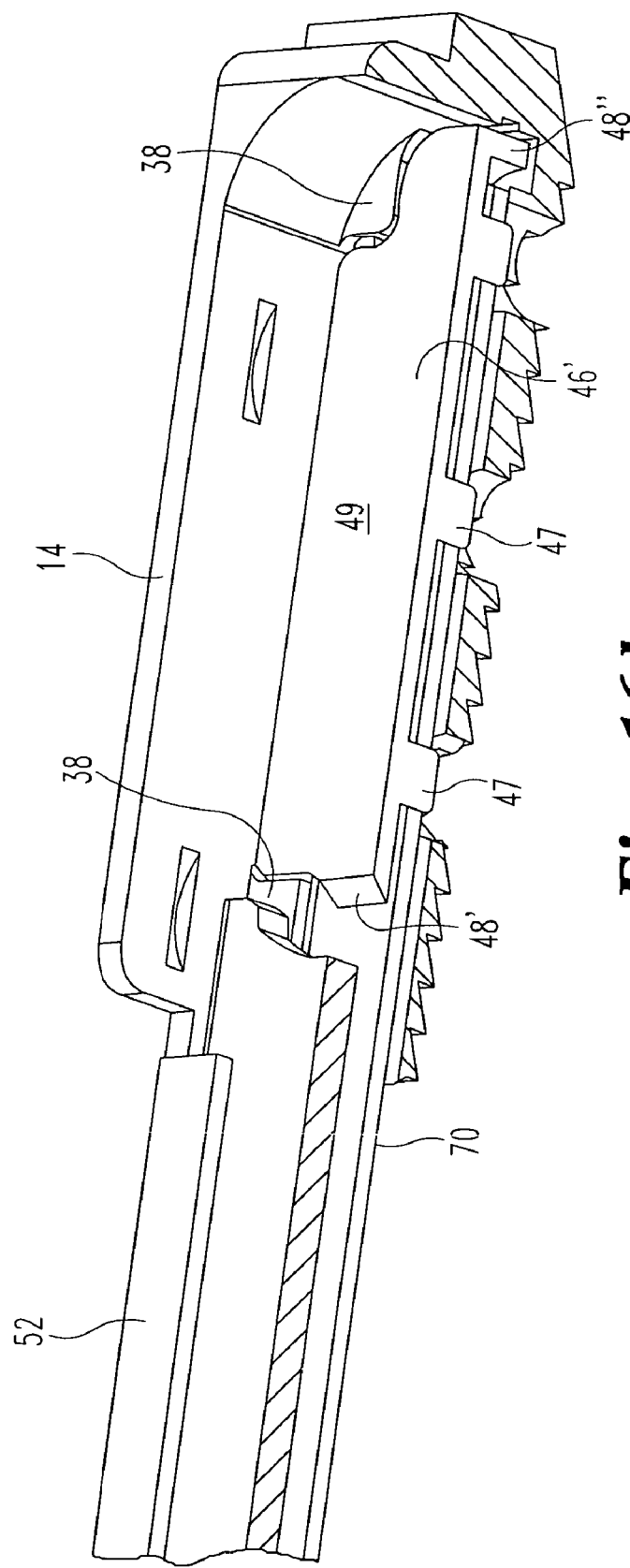
Figure 17:
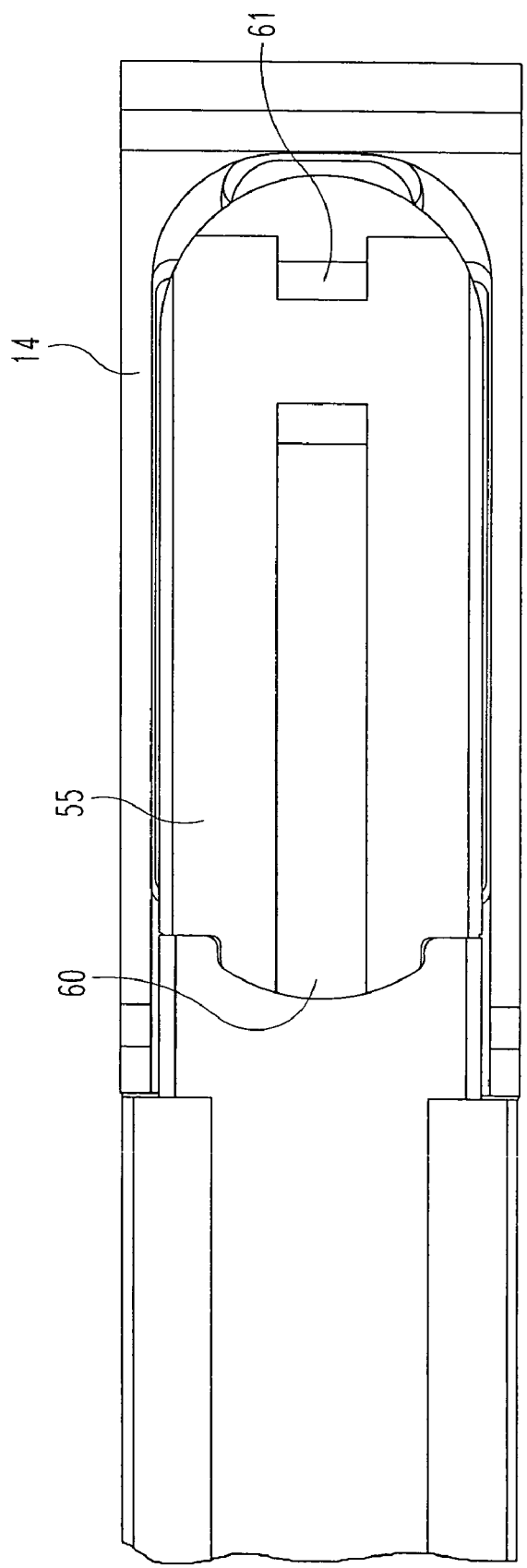
FIG. 17 is a top view of the insertion apparatus with a wafer situated within the inferior endplate portion of the IBFD. The superior endplate is removed to show the position of the wafer in the wafer cavity.
Figure 18:
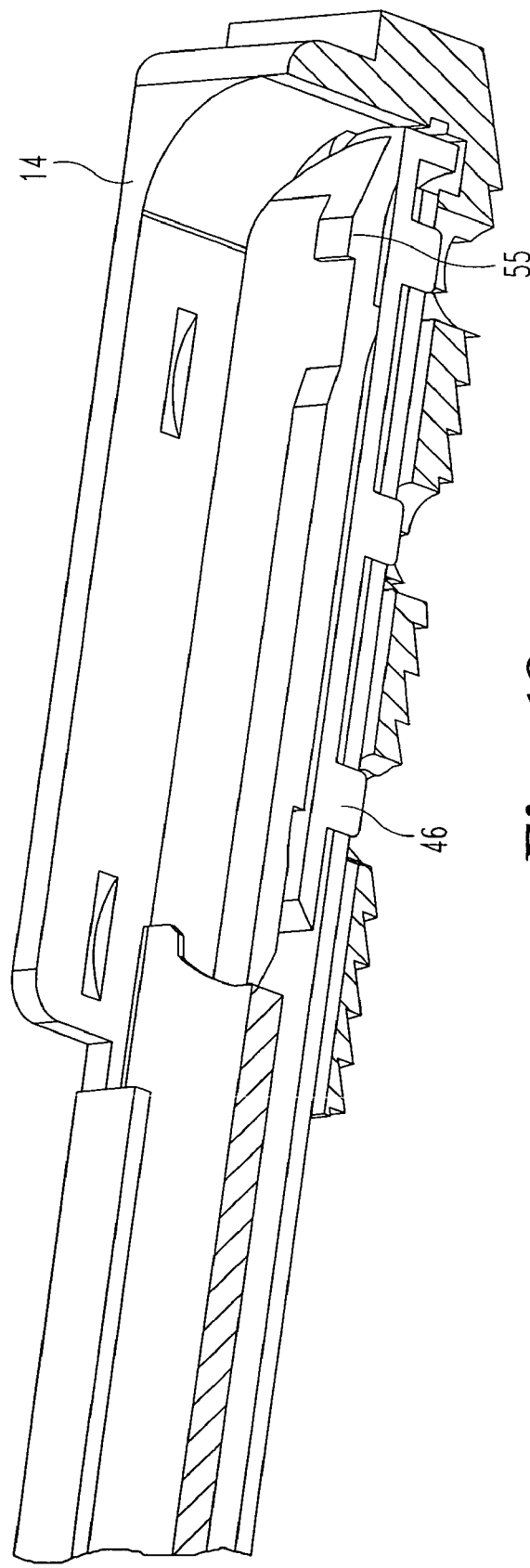
FIG. 18 is a perspective cut-away view of the insertion apparatus, the inferior endplate portion of the IBFD, including the track connector, and wafer shown in FIG. 17.
Figure 19:
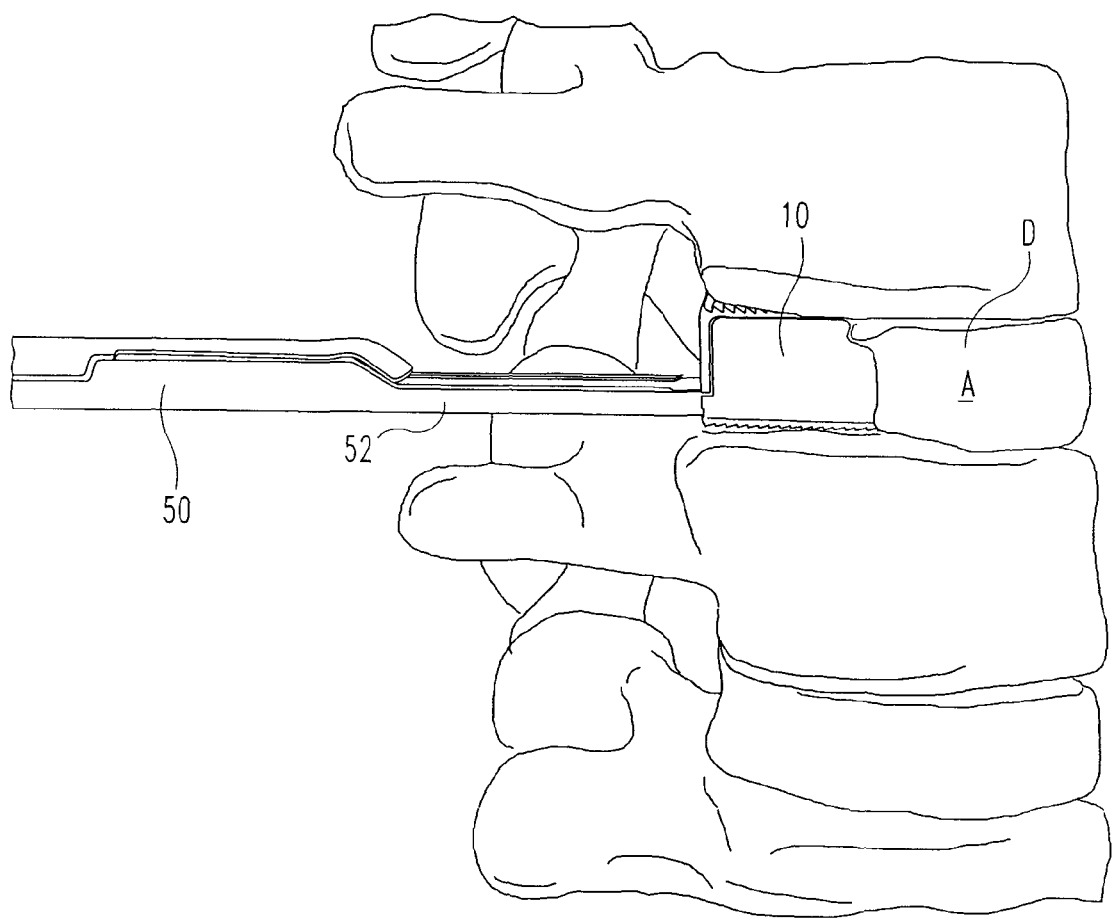
FIG. 19 is a side pictorial view of the insertion apparatus being used to insert an IBFD in accordance with the present invention into an intervertebral space.

The next series of figures, FIGS. 16a-d, show the placement of the track connector on top of the insertion plate 70 and release plate 75. As can be seen in FIG. 16d, the wafer support surface 49 is generally contiguous with wall 38 of the inferior endplate 14. In an alternate embodiment the wafer support surface 49 is superior to wall 38 of the inferior endplate 14. This alternate embodiment ensures that the compressive load from the wafer stack is transmitted through the wafer support surface 49 and not through wall 38. A first wafer 55 is added in FIGS. 17-18.

The inserter apparatus 50 and the IBFD 10 are shown in position for implanting the IBFD within an interbody space. It is contemplated that the interbody or intradiscal space will be prepared in a known manner. In particular, the disc nucleus is removed by known means, preferably leaving the disc annulus A relatively intact. A portal is formed in the annulus that is sized to the dimensions of the IBFD 10 in its unexpanded configuration (as shown in FIGS. 1-2).

Figure 20A:
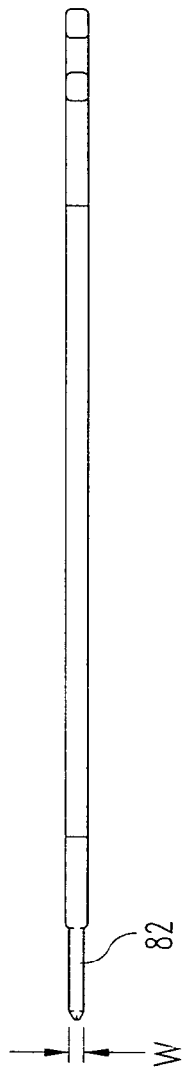
FIGS. 20a-20c include side, top and end views of a disc space distractor for use with the insertion apparatus shown in the above identified figures.
Figure 20B:
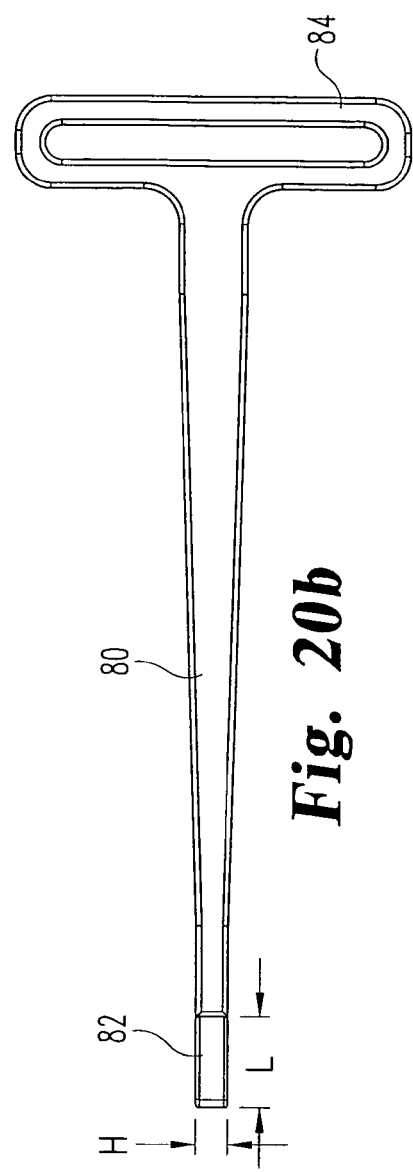
Figure 20C:
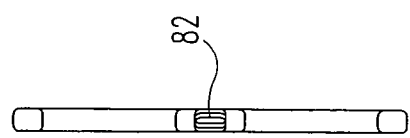
Figure 21B:
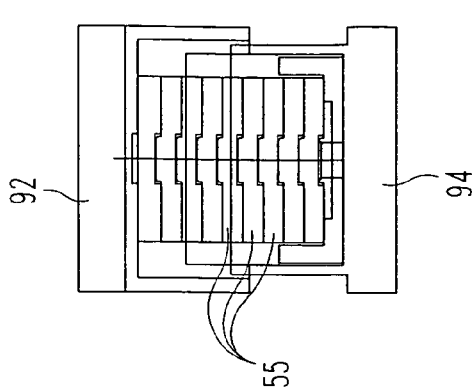
FIGS. 21a-21b are side and end cross-sectional views of an IBFD in accordance with one embodiment of the present invention with a stack of wafers introduced therein to one pre-determined height.
Figure 21D:
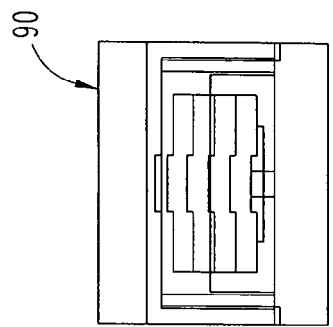
FIGS. 21c-21d are side and end cross-sectional views of the IBFD shown in FIGS. 21a-21b stacked to a different height in which all of the wafers are contained within the endplates.
Figure 21A:
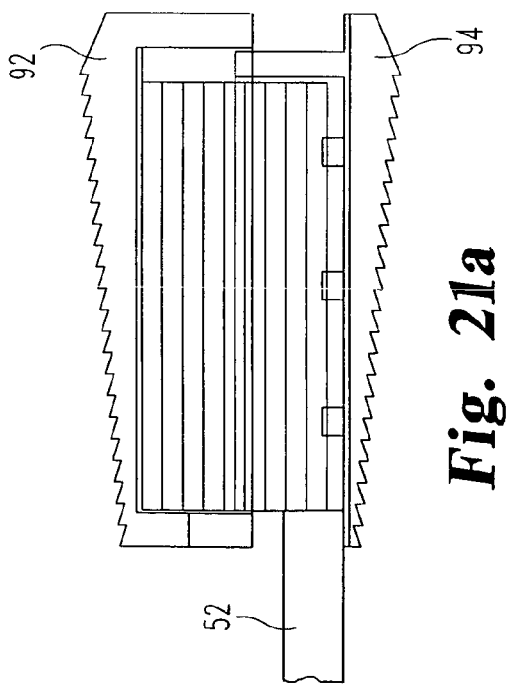
Figure 21C:
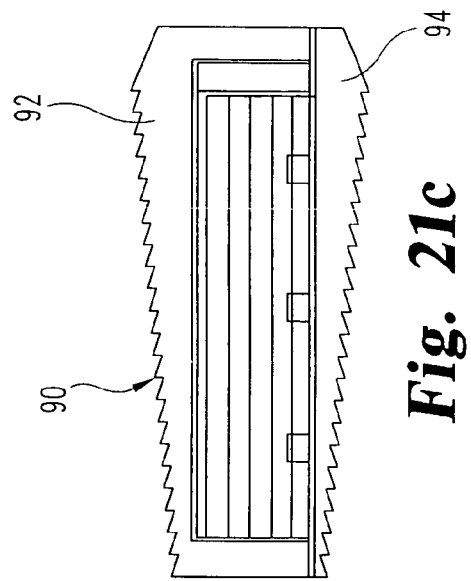
Figure 22B:
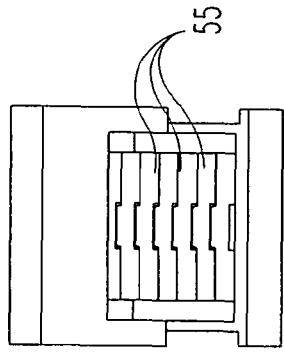
FIGS. 22a-d include side and end views of the IBFD shown in FIGS. 21a-21b.
Figure 22D:
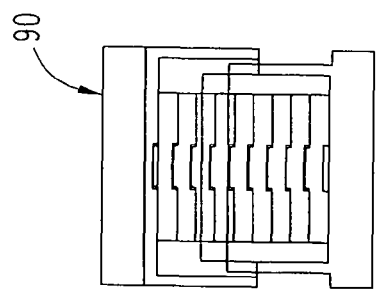
Figure 22A:
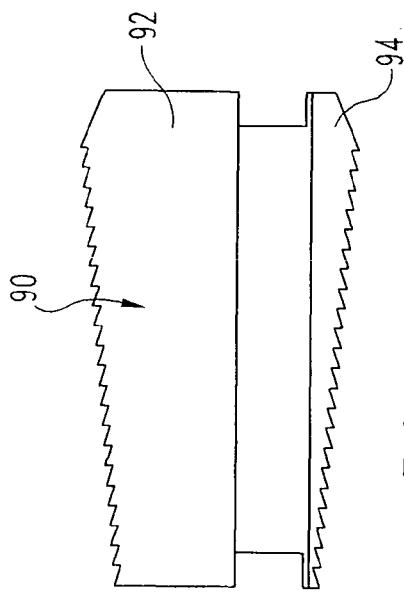
Figure 22C:
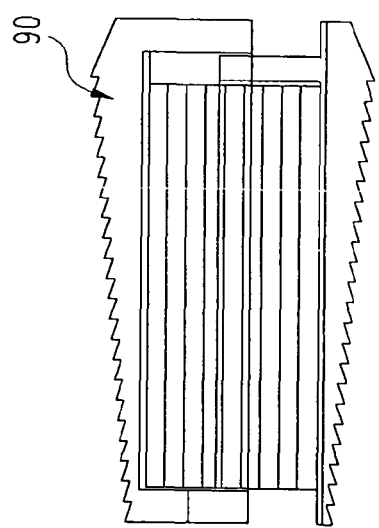
Figure 23A:
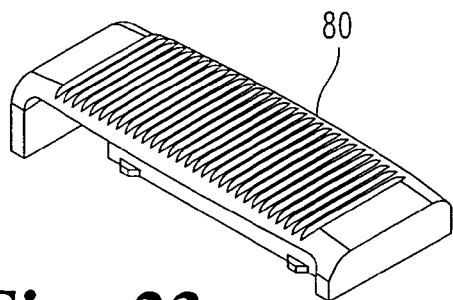
FIGS. 23a-23d include top and bottom perspective views, a side view and a cross-sectional view of a superior endplate for a sagittally curved embodiment of an IBFD of the present invention.
Figure 23B:
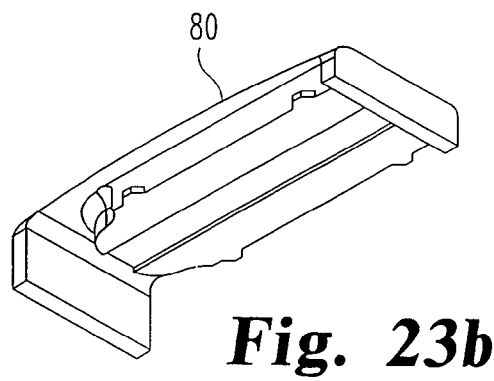
Figure 23C:
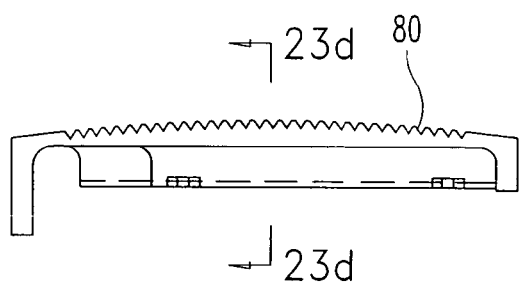
Figure 23D:
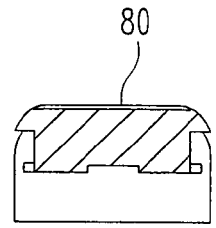
Figure 24A:
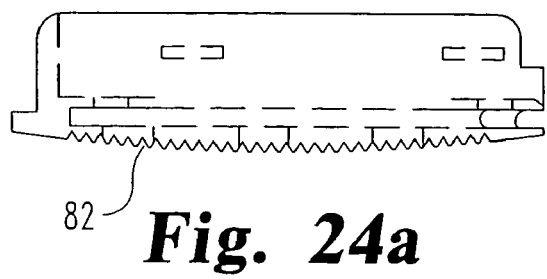
FIGS. 24a-24d include side, top perspective, top and end views of an inferior endplate for a sagittally curved embodiment of an IBFD of the present invention.
Figure 24B:
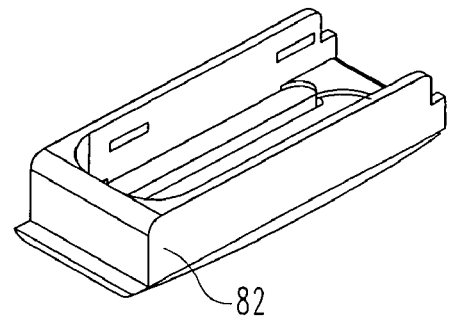
Figure 24C:
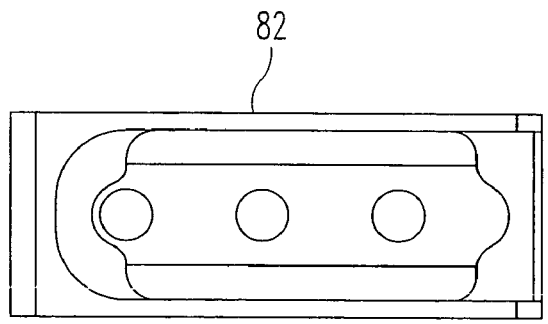
Figure 24D:
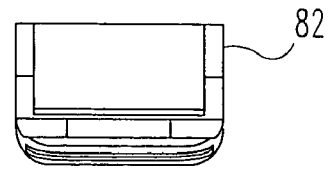

In the preferred arrangement, the IBFD is sized to be received in the unexpanded state through the portal into the disc space without any pre-distraction. In certain situations where the disc space height is smaller than the height of the unexpanded IBFD, pre-distraction may be used to slightly elevate the disc space so as to allow receipt of the unexpanded IBFD through the portal. Such pre-distraction, which can occur using conventional techniques, is not intended to achieve the final disc space height. One approach is to use the distractor 80 shown in FIGS. 20a-20c. This distractor includes a distal end 82 having a height H greater than its width W. The height H of the distal end 82 is substantially constant over the insertion length L. The distractor is inserted into the disc space at a location adjacent to but laterally spaced from the location where the IBFD is to be inserted with its larger dimension parallel to the vertebral endplates. As such, no distraction occurs during insertion of the distractor 80. The handle 84 is used to rotate the distractor 80 until the larger dimension contacts and pushes apart the vertebral endplates. The distractor 80 can be held in position as the IBFD is maneuvered into the interbody space using the inserter apparatus 50. After removal of the distractor, a second IBFD may be inserted adjacent to the first implanted IBFD.

As shown in FIGS. 21a-d and FIGS. 22a-d, the IBFD can be expanded to a specific height, with its height being determined by the number of wafers 55 inserted into the IBFD. In the preferred embodiment, the superior and inferior endplates 12, 14 and the wafers have a pre-determined height or thickness. As explained above, the endplates include overlapping portions to help stabilize the stack, in particular the end walls 24 and 32. After implanting the IBFD a biomaterial, such as bone chips or other osteogenetic materials, such as bone morphogenic proteins or adipose-derived adult stromal cells, may be introduced adjacent to or in contact with the IBFD so as to promote fusion between the opposing vertebrae.

As indicated in the figures, in certain embodiments of the invention, the stack height will change when the inserter apparatus is dislodged from the IBFD and removed. In particular, the wafer stack will shift slightly downward when the insertion plate and release plates are removed, allowing the track connector 46 to drop down.

The IBFD 90 shown in FIGS. 21a-d and FIGS. 22a-d includes superior and inferior endplates 92, 94 that are angled. These endplates are configured to restore or maintain a particular angle of the vertebral motion segment. For instance, if the IBFD 90 is used in the lumbar spine, the endplates are defined at a lordotic angle. The endplates 80, 82 in FIGS. 23a-d and FIGS. 24a-d are also configured to have arcuate upper and lower surfaces for introduction into and anatomical support of the lumbar spine.

Figure 25A:
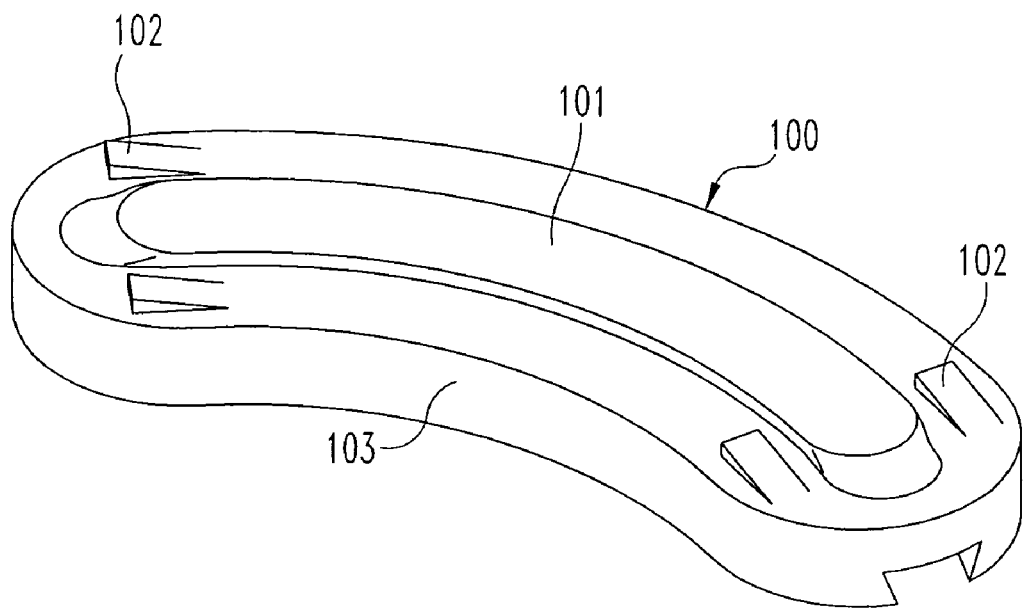
FIGS. 25a-c are perspective, top and cross-sectional views of a transversely curved wafer for use with an IBFD of the present invention.
Figure 25B:
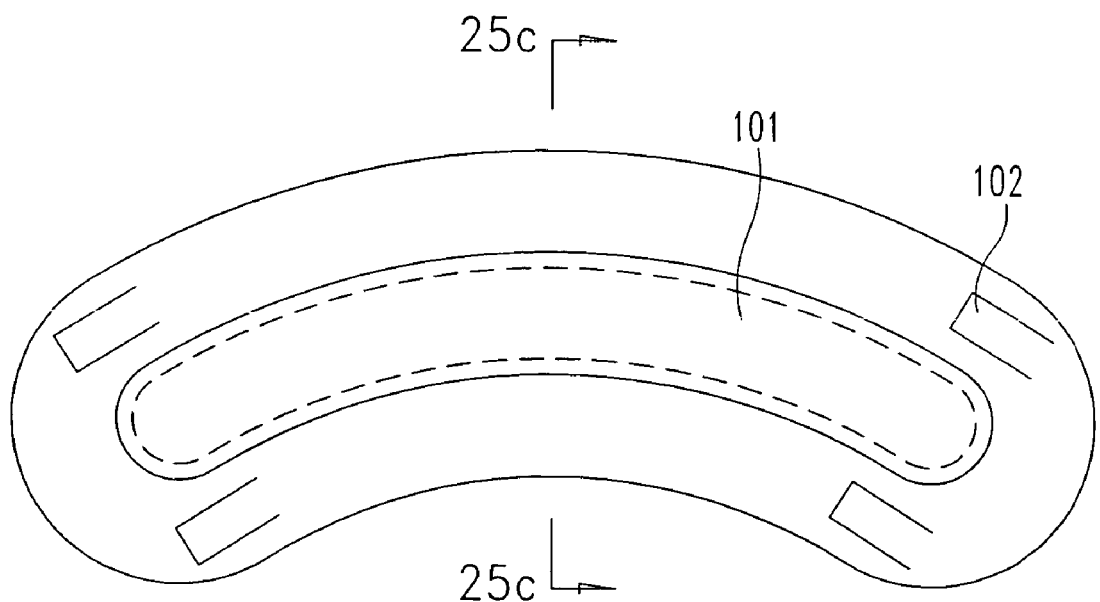
Figure 25C:
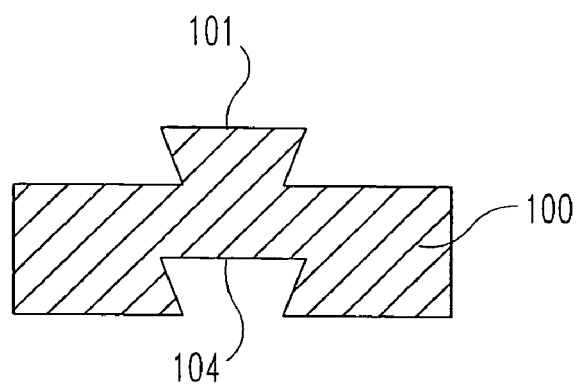
Figure 26:
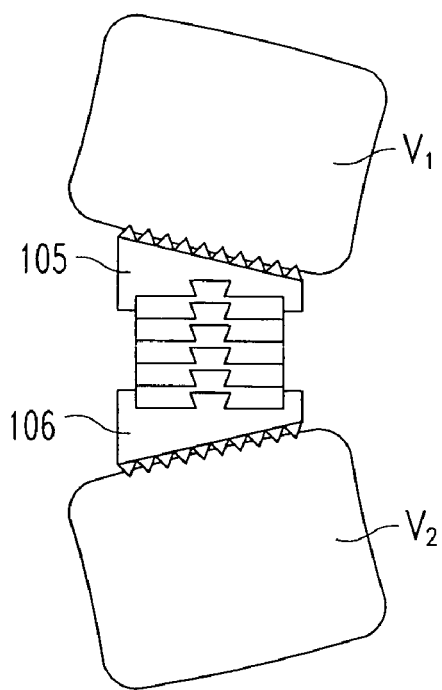
FIG. 26 is a side representation of an IBFD implanted in an intervertebral space with wafers as shown in FIGS. 25a-c.

Alternative concepts for the endplates and the wafers are shown in FIGS. 25a-27d. In FIGS. 25a-c, a curved wafer 100 is provided. The wafer includes interlocking dovetail features 101 and 104 and locking notches 102 to help hold the wafer stack together. As shown in FIG. 26, the endplates 105, 106 can be angled to restore the lordotic angle of the motion segment with the wafer stack therebetween.

Figure 27A:
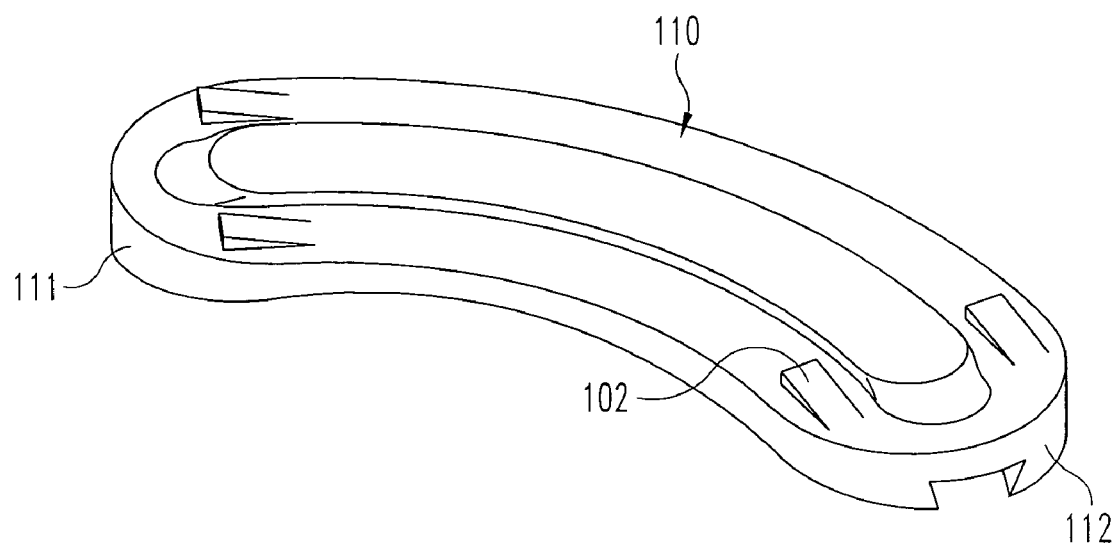
FIGS. 27a-c are perspective, top and cross-sectional views of a transversely curved and angled wafer for use with an IBFD of the present invention.
Figure 27B:
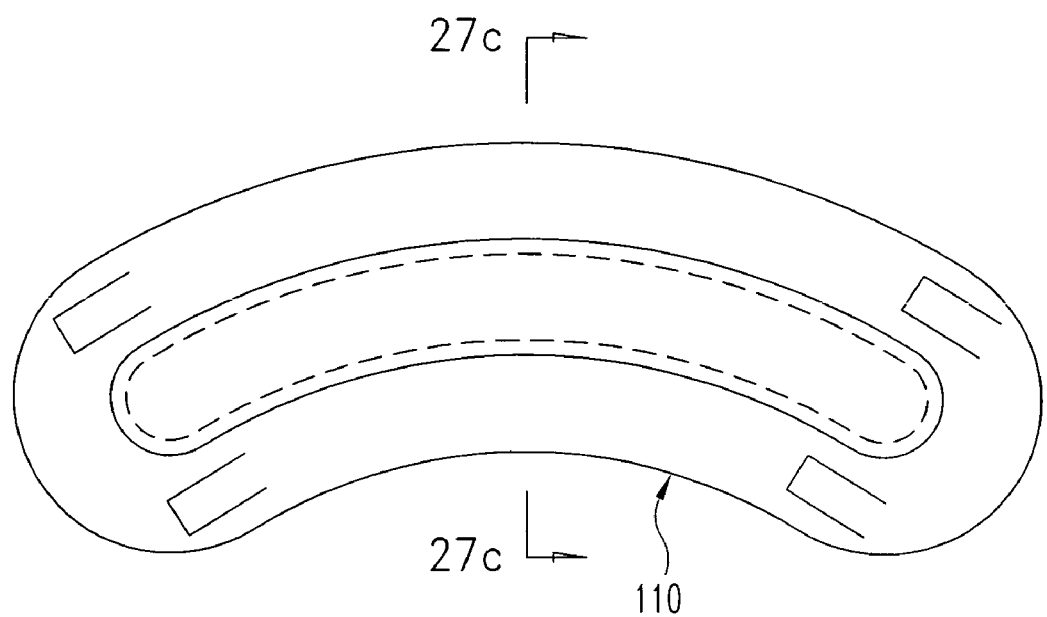
Figure 27C:
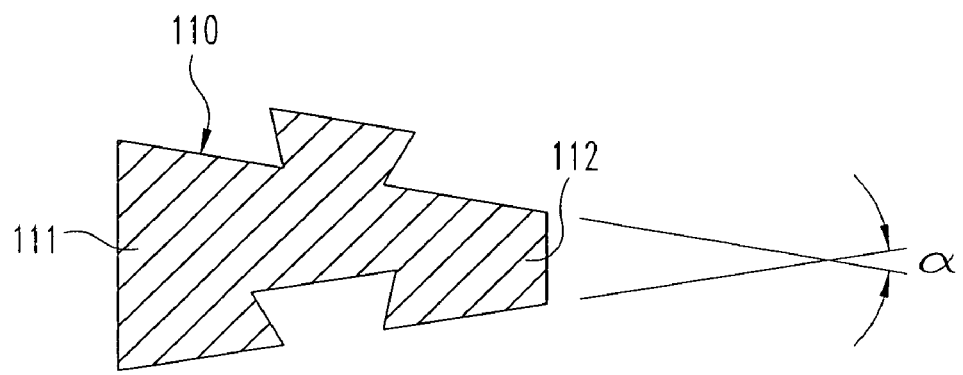
Figure 27D:
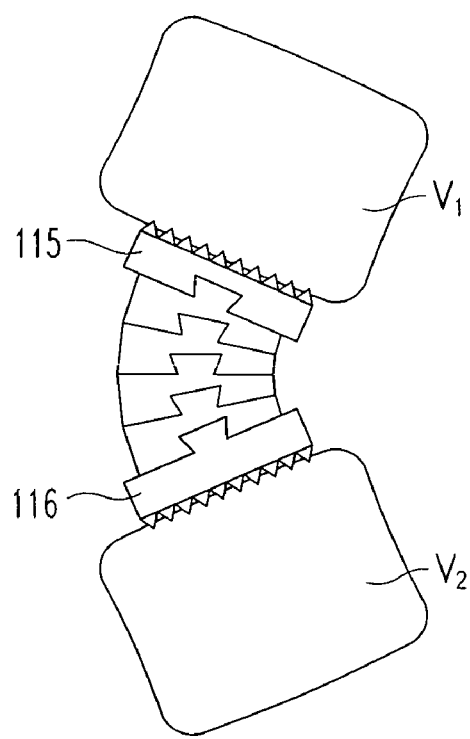
FIG. 27d is a side representation of an IBFD implanted in an intervertebral space with wafers as shown in FIGS. 27a-c.

As an alternative, the wafers can provide the lordotic angle, such as the wafer 110 shown in FIGS. 27a-c. The wafer 110 includes one end 111 that is thicker than the opposite end 112. The wafers can be contained within endplates 115, 116 that are planar—i.e., that do not incorporate the lordotic angle.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

This invention contemplates an interbody fusion device configured for implantation within an interbody space that incorporates a cavity for receipt of bio-compatible wafers. The wafers can be used to fill the cavity and provide additional strength for the IBFD components, and to increase the height of the IBFD. In this way, a smaller IBFD can be initially introduced into the interbody space, preferably minimally invasively, and then a series of wafers can be introduced to incrementally increase the height of the IBFD in situ, to thereby increase the disc space substantially to its natural height.

What is claimed is:

1. An apparatus for use in restoring the anatomical height of a damaged or diseased disc space between two opposing vertebral bodies in a spine, comprising:
   a) an expandable interbody fusion device comprising:
      a superior elongate endplate member having an upper surface for engaging a superior vertebral body in a spine, an opposite lower surface and opposing side surfaces;
      an inferior elongate endplate member having a lower surface for engaging an inferior vertebral body in said spine and spaced opposing side surfaces, said superior endplate member and said inferior endplate member being releasably coupled to each other along said side surfaces of each said member; and
      at least one expansion member configured to be introduced between said superior endplate member and said inferior endplate member to move said members relatively apart upon introduction and to thereby decouple the side surfaces of said superior endplate member and said inferior endplate member, said at least one expansion member having an upper surface and together with said lower surface of said superior endplate member further defining a cooperative engagement interlocking said expansion member and said superior endplate member upon said introduction of said expansion member; and
   b) an inserter releasably connected to said fusion device, said inserter including a track defining a channel through which said expansion element is conveyed for introduction into said fusion device, there being a separable interface between said track and said fusion device, said interface comprising a connector plate supported by said inferior endplate member, said connector late including a support surface on one side for supporting said expansion member and at least one severable member on an opposite side for temporarily holding said track to said fusion device.

2. The apparatus of claim 1, wherein said opposing side surfaces of said inferior endplate member are respectively defined by a pair of opposing spaced apart sidewalls projecting upwardly from said lower surface, said projecting sidewalls of said inferior endplate member configured to decouple with the side surfaces of said superior endplate member as said superior endplate member and said inferior endplate member are moved apart.

3. The apparatus of claim 2, wherein said opposing side surfaces of said superior endplate member are respectively defined by a pair of opposing spaced apart sidewalls depending downwardly from said upper surface.

4. The apparatus of claim 2, wherein said inferior endplate member has at least one end wall projecting upwardly from said lower surface.

5. The apparatus of claim 1, wherein said releasable coupling includes at least one of said side surfaces of one of said superior endplate member or said inferior endplate member having a projecting prong and the side surface of the other of said superior endplate member or said inferior endplate member defining a complementary notch for receipt of said prong.

6. The apparatus of claim 5, wherein said superior endplate member has at least one end wall depending downwardly from said upper surface.

7. The apparatus of claim 1, wherein said upper surface of said superior endplate member and said lower surface of said inferior endplate member each comprise gripping surfaces for engagement with the respective superior and interior vertebral bodies.

8. The apparatus of claim 7, wherein said gripping surfaces are defined by ribs having a generally saw-toothed configuration.

9. The apparatus of claim 1, wherein at least one of said upper surface of said superior endplate member or said lower surface of said inferior endplate member is angled to provide a particular angle between said opposing vertebral bodies.

10. The apparatus of claim 9, wherein both said upper surface of said superior endplate member and said lower surface of said inferior member are angled.

11. The apparatus of claim 1, wherein at least one of said upper surface of said superior endplate member or said lower surface of said inferior endplate member is arcuate to provide anatomical support of the vertebral bodies.

12. The apparatus of claim 11, wherein both of said upper surface of said superior endplate member and said lower surface of said inferior member are arcuate.

13. The apparatus of claim 1, wherein said at least one expansion member is a generally flat wafer configured for sliding insertion under sufficient pressure to move said superior endplate member and said inferior endplate member apart.

14. The apparatus of claim 13, wherein the apparatus comprises a plurality of wafers slidably received in contact to form a stack of wafers between said superior endplate member and said inferior endplate member.

15. The apparatus of claim 14, wherein each of said wafers has an upper generally flat surface and a lower generally flat surface.

16. The apparatus of claim 15, wherein the lower flat surface of a wafer in said stack and the upper flat surface of a contacting wafer comprise complementary interdigitating configurations to provide at least lateral and rotational stability to said stack of wafers.

17. The apparatus of claim 16, wherein said complementary configurations are defined by a ridge on at least one of said wafer surfaces and a trough on the other of said wafer surfaces for receiving said ridge.

18. The apparatus of claim 14, wherein said wafers comprise complementary interdigitating configurations to provide at least lateral and rotational stability to said stack of wafers.

19. The apparatus of claim 1, wherein said superior endplate member and said inferior endplate member are each formed of biocompatible material.

20. The apparatus of claim 1, wherein said opposing side surfaces of said superior endplate member overlap with said spaced opposing side surfaces of said inferior endplate member and define said releasable coupling therebetween.

21. The apparatus of claim 20, wherein said releasable coupling is defined by a prong on one of said overlapping side surfaces and a complementary notch on the other of said overlapping side surfaces.

22. The apparatus of claim 1, further including a movable release plate supported by said track and having a cutting surface operable upon movement to sever said at least one severable member on said connector plate, to thereby allow removal of said track from said fusion device.

23. The apparatus of claim 22, wherein there are at least two severable members on said connector plate and wherein said release plate has at least two openings for respectively receiving said severable members.

24. The apparatus of claim 23, wherein the edges of said openings in said release plate define said cutting surfaces.

25. The apparatus of claim 24, wherein one of said openings is elongate relative to the other of said openings to thereby cause cutting of said severable members in a sequential manner upon movement of said release plate.

26. The apparatus of claim 1, wherein said device comprises a plurality of expansion members, each being a generally flat wafer and configured for slidable receipt to form a stack of wafers within said device.

* * * * *